United States Patent
Yu et al.

(10) Patent No.: US 9,390,514 B2
(45) Date of Patent: Jul. 12, 2016

(54) IMAGE BASED TRACKING

(75) Inventors: Weichuan Yu, Hong Kong (CN);
Tianzhu Liang, Hong Kong (CN);
Xiaowei Zhou, Hong Kong (CN)

(73) Assignee: The Hong Kong University of Science and Technology, Kowloon (HK)

( * ) Notice: Subject to any disclaimer, the term of this patent is extended or adjusted under 35 U.S.C. 154(b) by 396 days.

(21) Appl. No.: 14/125,067

(22) PCT Filed: Jun. 7, 2012

(86) PCT No.: PCT/CN2012/000782
§ 371 (c)(1),
(2), (4) Date: Dec. 9, 2013

(87) PCT Pub. No.: WO2012/167616
PCT Pub. Date: Dec. 13, 2012

(65) Prior Publication Data
US 2014/0112544 A1    Apr. 24, 2014

Related U.S. Application Data

(60) Provisional application No. 61/457,813, filed on Jun. 9, 2011, provisional application No. 61/631,815, filed on Jan. 12, 2012.

(51) Int. Cl.
*G06T 7/00* (2006.01)
*G06T 7/20* (2006.01)
(Continued)

(52) U.S. Cl.
CPC ............... *G06T 7/2033* (2013.01); *A61B 8/565* (2013.01); *A61B 8/587* (2013.01); *G06K 9/6201* (2013.01);
(Continued)

(58) Field of Classification Search
None
See application file for complete search history.

(56) References Cited

U.S. PATENT DOCUMENTS 6,574,353 B1 *  6/2003  Schoepflin  ........... G06K 9/6206
                                           348/169
6,807,536 B2 * 10/2004  Achlioptas ........... G06K 9/6247
                                           324/303

(Continued)

FOREIGN PATENT DOCUMENTS

CN       1509456 A       6/2004
CN       101567051 A    10/2009

OTHER PUBLICATIONS

Nkomo et al. "Burden of valvular heart diseases: a population-based study." The Lancet, 368(9540), Sep. 16, 2006, pp. 1005-1011.
(Continued)

*Primary Examiner* — Nirav G Patel
*Assistant Examiner* — Alexander J Lesnick
(74) *Attorney, Agent, or Firm* — Amin, Turocy & Watson, LLP

(57) ABSTRACT

Systems and methods that facilitate image motion analysis are described herein. According to a first image motion analysis technique a first image is warped according to a locally affine model. The first warped image and a second image are compared and a match between the first warped image and the second image is discovered. A value for a motion parameter is estimated based on the match. According to a second image motion analysis technique, an image sequence is converted into an input matrix. A column of the input matrix corresponds to a vectorized image related to the image sequence. The input matrix is approximated with a low rank matrix having a lower rank than the input matrix. One or more outliers of the input matrix are detected.

20 Claims, 28 Drawing Sheets

(51) Int. Cl.
   *G06K 9/62* (2006.01)
   *G06T 3/00* (2006.01)
   *A61B 8/00* (2006.01)
   *A61B 8/08* (2006.01)
(52) U.S. Cl.
   CPC .............. *G06T 3/0093* (2013.01); *G06T 7/0012* (2013.01); *G06T 7/208* (2013.01); *G06T 7/2046* (2013.01); *A61B 8/0883* (2013.01); *A61B 8/485* (2013.01); *G06T 2207/10016* (2013.01); *G06T 2207/10132* (2013.01); *G06T 2207/30048* (2013.01)

(56) References Cited

U.S. PATENT DOCUMENTS

| | | | |
|---|---|---|---|
| H002222 H * | 8/2008 | Rangaswamy | 342/159 |
| 8,959,128 B1 * | 2/2015 | Strelow | G06F 7/38 708/200 |
| 2012/0134588 A1 * | 5/2012 | Zhang | G06K 9/3275 382/176 |

OTHER PUBLICATIONS

Hung et al. "3D Echocardiography: A Review of the Current Status and Future Directions." Journal of the American Society of Echocardiography; vol. 20, No. 3. Mar. 2007, pp. 213-233.
Yilmaz et al. "Object Tracking: A Survey." ACM Computing Surveys, vol. 38, No. 4, Article 13. Dec. 2006, 45 pages.
Noble et al. "Ultrasound Image Segmentation: A Survey." IEEE Transactions on Medical Imaging, vol. 25, No. 8, Aug. 2006, pp. 987-1010.
Beauchemin, et al. "The Computation of Optical Flow." ACM Computing Surveys, vol. 27, No. 3, Sep. 1995, pp. 433-467.
Meunier et al. "Ultrasonic texture motion analysis: theory and simulation." IEEE Transactions on Medical Imaging, vol. 14. No. 2, Jun. 1995, pp. 293-300.
Blake et al. "Active contours: The Application of Techniques from Graphics, Vision, Control Theory and Statistics to Visual Tracking of Shapes in Motion." Springer, 1998, 361 pages.
Mikic et al. "Segmentation and Tracking in Echocardiographic Sequences: Active Contours Guided by Optical Flow Estimates." IEEE Transactions on Medical Imaging, vol. 17, No. 2, Apr. 1998, pp. 274-284.
Shang et al. "Region competition based active contour for medical object extraction." Computerized Medical Imaging and Graphics 32 (2008) pp. 109-117.
Burlina et al. "Patient-Specific Modeling and Analysis of the Mitral Valve Using 3D-TEE." Information Processing in Computer-Assisted Interventions 2010, LNCS 6135, 2010, pp. 135-146.
Schneider et al. "Mitral Annulus Segmentation from 3D Ultrasound Using Graph Cuts." IEEE Trans Med Imaging. Sep. 2010; 29(9): 1676-1687.
Schneider et al. "Patient-Specific Mitral Leaflet Segmentation from 4D Ultrasound." Med Image Comput Comput Assist Interv. Oct. 25, 2011; 14(Pt 3): 520-527.
Ionasec et al. "Patient-Specific Modeling and Quantification of the Aortic and Mitral Valves from 4D Cardiac CT and TEE." IEEE Transactions on Medical Imaging, 29(9): 2010, 1636-1651.
Recht et al. "Guaranteed Minimum-Rank Solutions of Linear Matrix Equations via Nuclear Norm Minimization." SIAM Review, 52(3), Jul. 19, 2007, 32 pages.
Mazumder et al. "Spectral Regularization Algorithms for Learning Large Incomplete Matrices." Journal of Machine Learning Research 11, Aug. 2010, 2287-2322.
Boykov et al. "Fast Approximate Energy Minimization via Graph Cuts." IEEE Trans. on Pattern Analysis and Machine Intelligence, 23(11), 2001, pp. 1222-1239.
Kolmogorov et al. "What Energy Functions Can Be Minimized via Graph Cuts?" IEEE Transactions on Pattern Analysis and Machine Intelligence, vol. 26, No. 2, Feb. 2004, pp. 147-159.

Ophir et al. "Elastography: ultrasonic estimation and imaging of the elastic properties of tissues." Proc Instn Mech Engrs vol. 213 Part H, Jan. 27, 1999, pp. 203-233.
Bercoff, et al. "Supersonic Shear Imaging: A New Technique for Soft Tissue Elasticity Mapping." IEEE Transactions on Ultrasonics, Ferroelectrics, and Frequency Control, vol. 51, No. 4, Apr. 2004, pp. 396-409.
Jahne, et al. "Motion." Handbook of Computer Vision and Applications, Chapter 13, 1st ed. Academic Press, 1999, vol. 2, pp. 309-396.
Richard Szeliski. "Dense motion estimation." Computer Vision: Algorithms and Applications, Chapter 8, 2010, pp. 381-426.
Trahey et al. "Angle independent ultrasonic detection of blood flow." IEEE Transactions on Biomedical Engineering, vol. BME-34, No. 12, Dec. 1987, pp. 965-967.
Meunier et al. "Echographic image mean gray level changes with tissue dynamics: A system-based model study," IEEE Transactions on Biomedical Engineering, vol. 42, No. 4, Apr. 1995, pp. 403-410.
J. Meunier. "Tissue motion assessment from 3D echographic speckle tracking." Phys. Med. Biol. 43 (1998) 1241-1254.
Yu et al. "Towards pointwise motion tracking in echocardiographic images: comparing the reliability of different features for speckle tracking." Medical Image Analysis, vol. 10, Mar. 30, 2006, pp. 495-508.
Lubinski et al. "Adaptive Strain Estimation Using Retrospective Processing." IEEE Transactions on Ultrasonics, Ferroelectrics, and Frequency Control, vol. 46, No. 1, Jan. 1999, pp. 97-107.
Lee et al. "In vivo study of myocardial elastography under graded ischemia conditions." Physics in Medicine and Biology, 56 (Feb. 1, 2011) pp. 1155-1172.
Pellot-Barakat et al. "Ultrasound Elastography Based on Multiscale Estimations of Regularized Displacement Fields." IEEE Trans Med Imaging, Feb. 2004; 23(2): pp. 153-163.
Yeung et al. "Feature-Adaptive Motion Tracking of Ultrasound Image Sequences Using a Deformable Mesh." IEEE Transactions on Medical Imaging, vol. 17, No. 6, Dec. 1998, pp. 945-956.
Chaturvedi et al. "2-D Companding for Noise Reduction in Strain Imaging." IEEE Transactions on Ultrasonics, Ferroelectrics, and Frequency Control, vol. 45, No. 1, Jan. 1998, pp. 179-191.
Insana et al. "3-D companding using linear arrays for improved strain imaging," in Proceedings of the IEEE Ultrasonics Symposium, vol. 2, 1997, pp. 1435-1438.
Alam et al. "Reduction of Signal Decorrelation from Mechanical Compression of Tissues by Temporal Stretching: Applications to Elastography." Ultrasound in Med. & Biol., vol. 23, No. 1, 1997, pp. 95-105.
Alam et al. "An Adaptive Strain Estimator for Elastography." IEEE Transactions on Ultrasonics, Ferroelectrics, and Frequency Control, vol. 45, No. 2, Mar. 1998, pp. 461-472.
Lubinski et al. "Speckle tracking methods for ultrasonic elasticity imaging using short-time correlation." IEEE Trans. on Ultrasonics, Ferroelectrics, and Frequency Control, vol. 46, No. 1, Jan. 1999, pp. 82-96.
Konofagou et al. "Spectral estimators in elastography." Ultrasonics 38 (2000) pp. 412-416.
Varghese et al. "Direct Strain Estimation in Elastography Using Spectral Cross-Correlation." Ultrasound in Med. & Biol., vol. 26, No. 9, 2000, pp. 1525-1537.
Chaturvedi et al. "Testing the Limitations of 2-D Companding for Strain Imaging Using Phantoms." IEEE Transactions on Ultrasonics, Ferroelectrics, and Frequency Control, vol. 45, No. 4, Jul. 1998, pp. 1022-1031.
Liang et al. "A coupled filtering method to solve featuremotion decorrelation in speckle tracking," in Proceedings of the IEEE International Symposium on Biomedical Imaging, Apr. 17, 2010, pp. 312-315.
Fleet et al. "Design and Use of Linear Models for Image Motion Analysis." International Journal of Computer Vision 36(3), 2000, pp. 171-193.
Jorgen Arendt Jensen. "A model for the propagation and scattering of ultrasound in tissue." J. Acoust. Soc. Am. 89 (1), Jan. 1991, pp. 182-190.

(56) References Cited

OTHER PUBLICATIONS

P. Anandan. "A Computational Framework and an Algorithm for the Measurement of Visual Motion." International Journal of Computer Vision, vol. 2, No. 3, 1989, pp. 283-310.

Burt et al. "The Laplacian Pyramid as a Compact Image Code." IEEE Transactions on Communications, vol. COM-31, No. 4, Apr. 1983, pp. 532-540.

International Search Report mailed Sep. 20, 2012 for International Application No. PCT/CN2012/000782, 3 pages.

* cited by examiner (A)          (B)

X-Z (two-chamber)    Y-Z (four-chamber)    X-Y (short-axis)    3-D

IMAGE BASED TRACKING

CROSS-REFERENCE TO RELATED APPLICATIONS

This application is a U.S. National Stage of PCT Application Serial No. PCT/CN2012/000782, entitled "IMAGE BASED TRACKING" and filed on Jun. 7, 2012, which claims priority to U.S. provisional application No. 61/457,813, entitled "An Affine Warping Method to Solve the Feature Motion Decorrelation Problem in Ultrasound Image Based Tracking" and filed on Jun. 9, 2011; and which also claims priority to U.S. provisional application No. 61/631,815, entitled "Method of Image Analysis Based on an Ultrasound Image Sequence for Automatic Mitral Leaflet Tracking" and filed on Jan. 12, 2012. The entireties of the aforementioned applications are herein incorporated by reference.

TECHNICAL FIELD

This disclosure generally relates to image analysis, and, more specifically, to facilitation of image motion analysis.

BACKGROUND

Mechanical properties of soft tissue correlate with various pathologies. For example: cancerous tissue is often stiffer than non-cancerous tissue; cirrhotic liver tissue is stiffer than normal liver tissue; and an ischemic heart often exhibits abnormal contraction/relaxation of myocardial tissues. The correlation between mechanical properties and pathologies can aid in the diagnosis of pathologies.

Elasticity imaging is a non-invasive method for measuring mechanical properties of soft tissue, which facilitates the diagnosis of various pathologies. Images are taken of soft tissue before and after application of a mechanical force. The images are correlated, and motion or deformation of the tissues can be inferred through a motion tracking algorithm.

An example of a motion tracking algorithm that can be used with elasticity imaging is speckle tracking. When the imaging modality is ultrasound imaging, speckles are formed when transmitted ultrasound waves are reflected by tissues and interfere with each other. Speckle tracking is based on the assumption that speckle patterns remain unchanged before and after tissue motion. The assumption that speckle patterns remain unchanged is used as the basis of motion tracking algorithms; however, speckle patterns do change after tissue deformation. Due to the change in speckle patterns after tissue deformation ("feature-motion decorrelation"), speckle tracking algorithms cannot reveal true tissue motion. Accordingly, speckle tracking algorithms lead to inaccurate estimation of tissue motion and improper inference of mechanical properties.

Motion tracking and geometry are also used in the diagnosis of various pathologies. For example, the mitral valve is a thin leaflet structure that lies between the left atrium and the left ventricle of the heart to control the direction of blood flow. Mitral valve related disease, such as mitral regurgitation, is the most common valvular heart disease. Imaging the heart and acquiring patient specific geometry features of the mitral valve, as well as tracking motion of the mitral valve, can facilitate diagnosis of valvular heart disease and/or assist with surgical intervention for valve repair.

Among various modalities, real time three dimensional echocardiography provides a noninvasive way to model the three dimensional geometry of the mitral valve and to capture its fast motion. To generate a comprehensive mitral valve model, the mitral leaflet is tracked throughout the echocardiographic sequence. To track an object, such as the mitral leaflet, the object is located and segmented throughout an image sequence. The location and segmentation of the mitral leaflet can be done manually, but manual delineation is both labor-intensive and prone to large variance. The variance is especially large for three dimensional images, when only two-dimensional projections or slices of volumetric data can be displayed and processed by the operator at a time. Tracking algorithms are able to track certain objects in natural image analysis. However, tracking the mitral leaflet is extremely difficult and no algorithms exist for such tracking. The mitral valve is especially hard to track due to a lack of reliable features, as well as fast and irregular valve motion.

The above-described background is merely intended to provide an overview of contextual information regarding motion tracking algorithms, and is not intended to be exhaustive. Additional context may become apparent upon review of one or more of the various non-limiting embodiments of the following detailed description.

SUMMARY

The following presents a simplified summary of the specification in order to provide a basic understanding of some aspects of the specification. This summary is not an extensive overview of the specification. It is intended to neither identify key or critical elements of the specification nor delineate any scope of particular embodiments of the specification, or any scope of the claims. Its sole purpose is to present some concepts of the specification in a simplified form as a prelude to the more detailed description that is presented later.

In accordance with one or more embodiments and corresponding disclosure, various non-limiting aspects are described in connection with facilitation of image motion analysis techniques. Non-limiting embodiments facilitate determination of mechanical properties with compensation of feature motion decorrelation. Further non-limiting embodiments facilitate object tracking through segmentation without user interaction or training data.

In accordance with a non-limiting aspect, systems and methods are described that facilitate determination of mechanical properties through elasticity imaging. According to a non-limiting embodiment, a system is described that includes an image warping component and an estimation component. The image warping component is configured to warp an image according to a locally affine model to produce a warped first image. The estimation component is configured to search for a pattern that matches between the warped first image and a second image as a function of a pre-defined matching measure. The estimation component is further configured to estimate a motion parameter based on the pattern. The system includes a memory that stores the components and a processor that facilitates execution of one or more of the components.

In a further non-limiting embodiment, a method is described that includes warping, by a system including a processor, an image according to a locally affine model to produce a warped first image. The method further includes searching, by the system, for a pattern that matches between the warped first image and a second image as a function of a pre-defined matching measure and estimating, by the system, a motion parameter based on the pattern.

In another non-limiting embodiment, a computer-readable storage medium is described that has computer-executable instructions stored thereon that, in response to execution, cause a device including a processor to perform operations.

The operations include at least: receiving a first image and a second image; initializing a motion parameter; warping the first image according to a locally affine model; searching for a match between the warped first image and the second image according to a pre-defined matching measure; and estimating a value for the motion parameter based on the match.

According to another non-limiting aspect, systems and methods are described that facilitate automatic object tracking without additional user interaction or training data. According to a non-limiting embodiment, a system is described that includes a conversion component that facilitates conversion of an image sequence to an input matrix that includes a column that is a vectorized image from the image sequence. The system also includes an approximation component configured to approximate the input matrix with a low rank matrix that has a lower rank than the input matrix. The system also includes a detection component configured to detect one or more outliers of the input matrix. The system includes a memory that stores the components and a processor that facilitates execution of one or more of the components.

In another non-limiting embodiment, a method is described that includes converting, by a system including a processor, an image sequence into an input matrix. A column of the input matrix is a vectorized image from the image sequence. The method also includes approximating, by the system, the input matrix with a low rank matrix with a lower rank than the input matrix. The method further includes detecting, by the system, one or more outliers of the input matrix.

In another non-limiting embodiment, a computer-readable storage medium is described that has computer-executable instructions stored thereon that, in response to execution, cause a device including a processor to perform operations. The operations include at least: converting an image sequence into an input matrix with column of the input matrix being a vectorized image from the image sequence; approximating the input matrix with a low rank matrix with a lower rank than the input matrix; and detecting one or more outliers of the input matrix.

The following description and the drawings set forth certain illustrative aspects of the specification. These aspects are indicative, however, of but a few of the various ways in which the various embodiments of the specification may be employed. Other aspects of the specification will become apparent from the following detailed description of the specification when considered in conjunction with the drawings.

BRIEF DESCRIPTION OF THE DRAWINGS

Numerous aspects and embodiments are set forth in the following detailed description, taken in conjunction with the accompanying drawings, in which like reference characters refer to like parts throughout, and in which.

DETAILED DESCRIPTION

Figure 1:
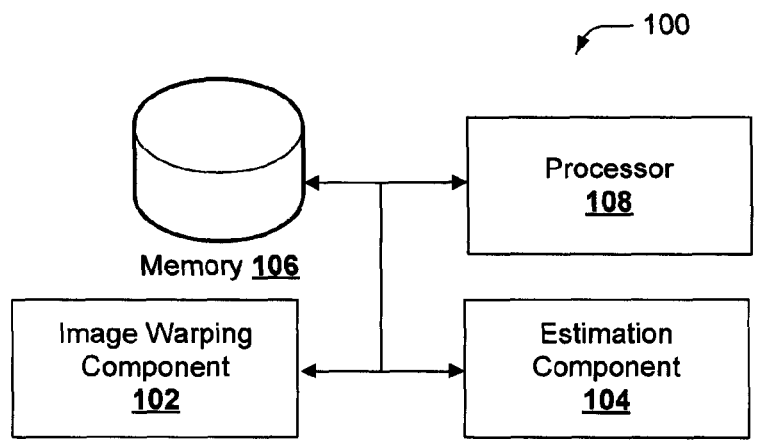
FIG. 1 illustrates an example non-limiting system that facilitates image analysis with compensation of feature motion decorrelation, according to an embodiment of the disclosure.

Various aspects or features of this disclosure are described with reference to the drawings, wherein like reference numerals are used to refer to like elements throughout. In this specification, numerous specific details are set forth in order to provide a thorough understanding of this disclosure. It should be understood, however, that the certain aspects of disclosure may be practiced without these specific details, or with other methods, components, materials, etc. In other instances, well-known structures and devices are shown in block diagram form to facilitate description and illustration of the various embodiments.

In accordance with one or more embodiments described in this disclosure, various non-limiting aspects are described in connection with image motion analysis techniques. Non-limiting embodiments facilitate determination of mechanical properties with compensation of feature motion decorrelation. Further non-limiting embodiments facilitate object tracking through segmentation without user interaction or training data.

Feature Motion Decorrelation

In accordance with one or more embodiments described in this disclosure, various non-limiting aspects are described in connection with determination of mechanical properties of an object with compensation of feature motion decorrelation. Feature motion decorrelation is compensated for through an affine warping process. A first image of the object is warped according to a locally affine model. The warped image and a second image of the object are compared, and a match between the warped image and the second image is discovered. A value for a motion parameter is estimated based on the match. The motion parameter can be used to facilitate determination of the mechanical properties.

Referring now to the drawings, with reference initially to FIG. 1, illustrated is an example non-limiting system 100 that facilitates image analysis through feature motion decorrelation, according to an embodiment of the disclosure. The system 100 can facilitate determination of mechanical properties of an object through elasticity imaging. Elasticity imaging facilitates determination of mechanical properties based on images taken of the object before application of a mechanical force to the object and after application of the mechanical force. The images can be ultrasound images, computed tomography images, magnetic resonance imaging images, or any other type of images or series of images. The images can be two dimensional images or three dimensional volumes.

The system 100 includes an image warping component 102 and an estimation component 104. The system also includes a memory that stores the components and a processor that facilitates execution of one or more of the components.

System 100, through the image warping component 102 and estimation component 104, solves the feature motion decorrelation problem. The feature motion decorrelation problem exists, in an embodiment, in ultrasound-based speckle tracking to facilitate determination of characteristics of motion of an object, such as tissue motion. In order to solve the problem of feature motion decorrelation, different models can be used to model sources of speckle variation.

Such variations may be caused by the complexity in tissues and their motion. Tissues may have diverse shapes and mechanical properties (e.g., generally cancerous tissues are stiffer than normal tissues, while tissues from different organs may have different mechanical properties, too). Thus, the interaction between tissues under mechanical forces is very complicated. Variations may also be caused by the nature of ultrasound images. Ultrasound images are formed when ultrasound waves interfere with each other after reflection. Therefore, when tissues undergo a complex motion, ultrasound waves will interfere differently to produce much more variant speckle patterns.

One model that can be used to solve the problem of feature motion decorrelation is a model that utilizes the companding method. The companding method which tries to model image variations caused by tissue deformation as a compression plus translation of the image. The method provides an effective approximation of the tissue deformation and is among the best methods in describing and compensating for image variations caused by tissue deformation, but the compensation of image variations will fail when tissue deformation is large.

Another modeling technique is the coupled filtering method. In the coupled filtering method, both the complex tissue motion and the nature of ultrasound images are modeled. A locally affine motion model is used to model the complex tissue motion and a linear convolution model is used to describe the interference of ultrasound waves during the imaging process.

The locally affine model is used to model complex tissue motion. For example, rigid/nonrigid motion of tissues is approximated as affine motion (e.g., compression or expansion) in a local area, while the local area is predefined before motion estimation or adjusted adaptively during motion estimation. Such a local motion can be estimated either in the spatial domain or in the spectral domain. Assuming that the tissue motion is affine in a local area, the complex tissue motion problem can be eliminated by a locally affine model:

$$x_n = MX_n + T,$$

where $X_n$ and $x_n$ are positions of the n-th tissue scatterer (according to an embodiment, an ultrasound-wave-reflecting tissue element) before and after the tissue motion, respectively. M is a matrix for the affine motion, while T is a vector for the tissue translation. In such a locally affine model, different kinds of tissue motion are modeled, such as translation, compression, expansion, shearing and rotation.

The local area in the local affine model can be predefined to be small enough so that the complex tissue motion can be approximated as affine motion in the area, while at the same time it should be large enough so that enough speckle patterns exist to recognize a matched pattern. Alternatively, the local area can be adjusted adaptively during the estimation of optimal motion parameters (in this case, optimal M and T). For example, the local area can be large at first so that a coarse estimation of optimal M and T is produced. Then the local area can be reduced and a refined estimation is produced.

Based on the local affine model, the displacement of tissues is also affine:

$$d_n = x_n - X_n = (M-I)X_n + T,$$

where $d_n$ is the displacement for the n-th tissue scatterer and I is an identity matrix with the same size as M. If the optimal motion parameters M and T are estimated accurately, the tissue motion in the local area is disclosed. Traditionally, if one further takes the derivative of $d_n$ with respect to $X_n$, strain values (e.g., normal strains and shear strains) as well as rotations can be estimated. Alternatively, since $d_n$ is an affine function of $X_n$, strain values and rotations are just a combination of the entries of matrix M, as shown in the infinitesimal strain theory. Direct deduction of strains and rotations from optimal motion parameters can be achieved in such way.

The linear convolution model is used to describe the interference of ultrasound waves during the imaging process. The formation of speckle pattern can be well described by the following linear convolution model:

$$I(X; X_n) = \sum_{n=1}^{N} T_n(X; X_n) * H(X),$$

where $T_n(X; X_n)$ is the n-th tissue scatterer, H(X) denotes the point spread function (PSF) of the ultrasound system, N is the total number of tissue scatterers, and $T(X; X_n)$ is the RF ultrasound image. The PSF of the ultrasound system can be interpreted as a linear system response function when only one tissue scatterer exists at the origin. The convolution model assumes that each tissue scatterer contributes independently and all tissue scatterers add up to produce a final ultrasound image.

In the linear convolution model above, each tissue scatterer can be modeled as a Dirac function:

$$T_n(X; X_n) = a_n \delta(X - X_n),$$

where again $X_n$ is the position of the n-th tissue scatterer and $a_n$ is reflectivity of the n-th tissue scatterer, showing how much percentage of ultrasound waves is reflected by the tissue scatterer. The PSF H(X) does not have an analytical expression in general. It depends on the ultrasound transducer (e.g., the shape and element arrangement of the ultrasound transducer, the central frequency and bandwidth of transmitted ultrasound waves, the scattering ability of tissues, etc.). In some literature, the PSF is approximated as a Gabor function. Alternatively, more accurate PSFs can be calculated numerically by solving acoustic wave equations based on different imaging settings.

Based on the locally affine motion model and the linear convolution model, the coupled filtering method proposes the ultrasound images before and after tissue motion read:

$$I(X; X_n) = \sum_{n=1}^{N} T_n(X; X_n) * H(X)$$

$$I(X; x_n) = \sum_{n=1}^{N} T_n(X; x_n) * H(X).$$

Since the positions of tissue scatterers have been changed, the interference pattern produced in the ultrasound images before and after tissue motion may be different. This will lead to the feature motion decorrelation problem. If decorrelation can be compensated, tissue motion can then reliably be estimated.

The compensation applied by the coupled filtering mechanism is based on the following equality relationship of the RF images taken before and after tissue motion:

$$I(MX + T; x_n) = \sum_{n=1}^{N} T_n(X; X_n) * H(MX)$$

-continued $$I(MX+T;x_n)*H(X) = \sum_{n=1}^{N} T_n(X;X_n)*H(MX)*H(X)$$
$$= I(X;X_n)*H(MX),$$

where $I(MX+T;x_n)$ denotes the affine warping result of the ultrasound image after tissue motion (i.e., the second image after applying an affine warping step), $I(MX+T;x_n)*H(X)$ denotes the coupled filtering result of the ultrasound image after tissue motion (i.e., the second image after applying an affine warping step and a coupled filtering step) and $I(X;X_n)*H(MX)$ denotes the coupled filtering result of the ultrasound image before tissue motion (i.e., the first image after applying a coupled filtering step). Based on the above relationship, one can thus find the optimal motion parameters M and T that best satisfy $$I(MX+T;x_n)*H(X) = \sum_{n=1}^{N} T_n(X;X_n)*H(MX)*H(X)$$
$$= I(X;X_n)*H(MX).$$

Strains and rotations can then be found directly or indirectly from the optimal motion parameters.

The coupled filtering method is able to estimate tissue motion accurately even when the tissue deformation is extremely large. However, in order to compensate variations of speckle patterns, the coupled filtering method involves both an affine warping step and a coupled filtering step before the search of matched patterns, which is very time consuming. Also, the coupled filtering method can only be applied to radio frequency (RF) ultrasound images, which is generally not available in clinical practice. Additionally, the coupled filtering method assumes the point spread function (PSF) is known and invariant in the linear convolution model, which is generally not the case in real applications. Therefore, it is desired to have a simple and robust method to solve the feature motion decorrelation issue in the B-mode (BM) ultrasound images.

System 100 applies an approximation of the coupled filtering method, affine warping. System 100 can apply affine warping to a pair of two dimensional or three dimensional, B-mode or radio frequency ultrasound images, one before the tissue motion and one after tissue motion. It should be noted that system 100 can also apply affine warping to a sequence of ultrasound images. For example, small tissue motion can be estimated for each pair of neighboring frames and accumulated to produce estimation of large deformation. Alternatively, tissue motion for each frame can also be estimated directly using the first frame as the reference.

System 100 facilitates application of affine warping through the image warping component 102 and the estimation component 104. The image warping component 102 can warp an image according to a locally affine model to produce a warped first image. The estimation component 104 is configured to search for a match between the warped first image and a second image as a function of a pre-defined matching measure. The estimation component is further configured to estimate a motion parameter based on the match.

The affine warping employed by system 100 is different from other methods that can reduce the feature motion decorrelation problem. The most related mechanism is the coupled filtering method. In the coupled filtering method, a locally affine motion model is used to model the complex tissue motion and a linear convolution model is used to describe the formation of ultrasound images as interference of ultrasound waves after reflection by tissues. In contrast, the affine warping employed by system 100 only uses the locally affine model to describe tissue motion. The interference of ultrasound waves during ultrasound image formation is ignored.

Affine warping employed by system 100 is different from the coupled filtering mechanism in that the compensation of speckle pattern variations is realized differently. With coupled filtering, an affine warping is applied to one of the two ultrasound images followed by applying two different filters to the two ultrasound images. System 100, in contrast, using affine warping, only warps one ultrasound image without a further filtering step, reducing the computational cost.

The affine warping method employed by system 100 employs an approximation of the coupled filtering method shown as follows:

$$I(MX+T;x_n)=I(X;X_n)$$

The approximation shown above is only an approximate relationship. The convolution operations in of the coupling filtering method are dropped. The remaining variation of speckle patterns may come from the variations of the PSF term. If the image variations from the tissue scatterer term are much larger than the variations from the PSF term, the approximation above provides a good approximation of the coupled filtering method.

The affine warping method is based on $I(MX+T;x_n)=I(X;X_n)$. As in the coupled filtering method, an affine warping step is applied to one of the two images before searching for matched patterns. No filtering step is applied. Accordingly, image warping component 102 warps an image according to a locally affine model to produce a warped first image without employing a filtering method before the estimation component 104 searches for a match between the warped first image and a second image as a function of a pre-defined matching measure.

The affine warping method obtains additional advantages over the coupled filtering method because it neither assumes a uniform PSF nor requires knowledge about the PSF. The affine warping method is not restricted to RF images and is able to work on B mode images as well. As the convolution operation has been dropped, the computation (e.g., by processor 108) is faster for the affine warping method compared to the coupled filtering method. In order to further accelerate the search of optimal motion parameters, different computational devices with differing processors 108 (e.g., multi-core CPU, workstations, clusters, GPUs, GPU clusters) can also be used.

Figure 2:
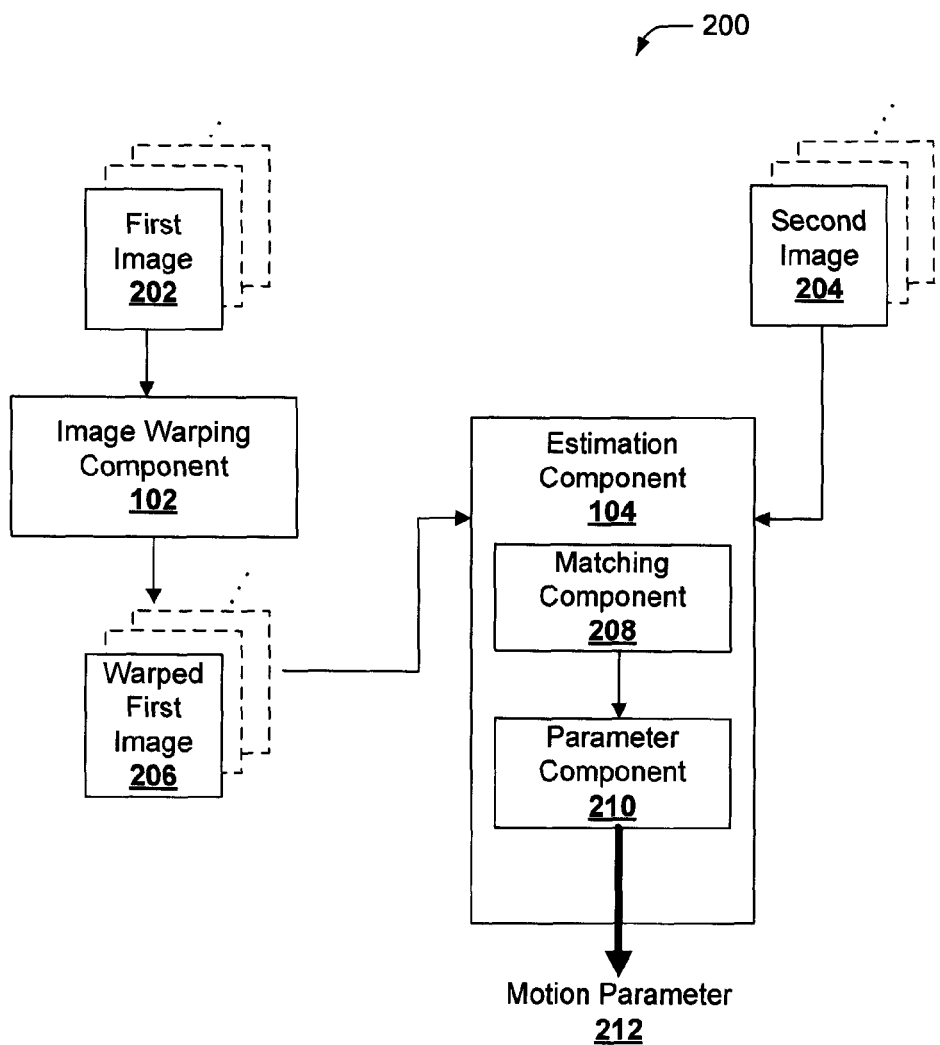
FIG. 2 illustrates an example non-limiting system that facilitates compensation of feature motion decorrelation, according to an embodiment of the disclosure.

Referring now to FIG. 2, illustrated is an example non-limiting system 200 that facilitates compensation of feature motion decorrelation through affine warping, according to an embodiment of the disclosure. A first image 202 and a second image 204 are fed into the system 200. In an embodiment, the first image 202 and the second image 204 can be sets of images. The first image and the second image can correspond to an image taken before application of a mechanical force and an image taken after application of the mechanical force. It will be understood that the definition of the first and second image as before and after mechanical force application does not matter. For example, the first image could be after application of the mechanical force and the second image could be before application of the mechanical force.

The image warping component warps 102 the first image 202 according to a locally affine model to produce a warped first image 206 (or warped first set of images). The warped first image 206 and the second image 204 are fed into the estimation component 104. The estimation component 104 searches for a match between the warped first image 206 and a second image 204 as a function of a pre-defined matching measure (matching component 208), and estimate a motion parameter based on the match (parameter component 210). The estimation component 104 can facilitate the estimation of tissue motion and the removal of tissue pattern variations caused by the tissue motion by applying an inverse motion field to the image to recover tissue motion.

The matching component 208 can employ one or more matching measures to find the match. The matching measures can include a correlation coefficient between the warped first image 206 and the second image 204, a sum of squared distance between the warped first image 206 and the second image 204, a sum of absolute distance between the warped first image 206 and the second image 204.

The parameter component 210 can facilitate the estimation of motion parameter. In an embodiment, the motion parameter can be M from the equation:

$$I(MX+T;x_n)=I(X;X_n)$$

In another embodiment, the motion parameter estimated can also include T.

Parameter component 210 can also include a constraint component that facilitates the estimation of the motion parameter according to one or more constraints. The constraint component can employ different mathematical models to better estimate tissue motion and compensate for speckle pattern variations caused by tissue motion.

In an embodiment, the constraints can relate to a property of an imaged object. The constraints can be smoothness constraints. When the object is biological tissue, the smoothness constraints ensure that the motion of neighboring tissues is similar. The constraints can also be deformation constraints. When the object is biological tissue, the smoothness constraints ensure that the motion of neighboring tissue is similar. The smoothness constraints assume that tissue motion at other positions can be interpolated from the motion of control points. When the object is biological tissue, the constraints can also be deformation constraints, which can relate to an incompressibility of the biological tissue.

Figure 3:
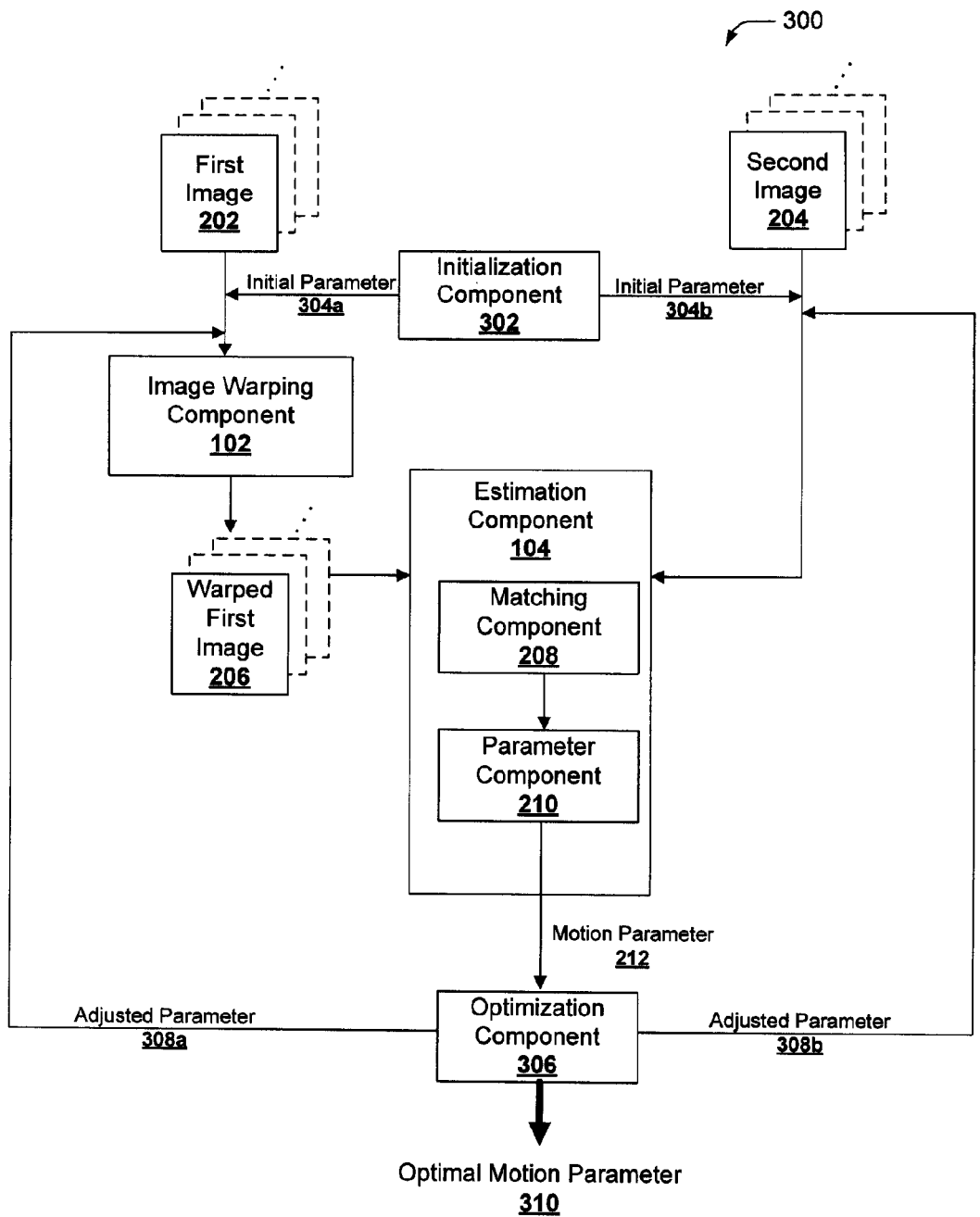
FIG. 3 illustrates an example non-limiting system that optimizes a motion parameter to facilitate compensation of feature motion decorrelation, according to an embodiment of the disclosure.

Referring now to FIG. 3, illustrated is an example non-limiting system 300 that optimizes a motion parameter to facilitate compensation of feature motion decorrelation, according to an embodiment of the disclosure. System 300 receives inputs of a first image 202 or set of images and a second image 204 or set of images. The first image 202 and the second image 204 can be taken before and after application of a mechanical force. If the object is biological tissue, the images can be taken before and after tissue motion.

The output of system 300 is an optimal motion parameter 310 or a set of optimal motion parameters (e.g., optimal M and T). The optimal motion parameter 310 enables an optimal compensation of speckle pattern variations. Normal strains, shear strains as well as rotation angles can then be estimated from the optimal motion parameter M based on the infinitesimal strain theory. In such cases, tissue motion is estimated directly, because strains and rotations are simple combinations of the entries of M. In RF images, such method achieves reasonably good results since enough high frequency components are available as unique features. However, for motion estimation in B mode images, a traditional indirect method is recommended, which calculates estimated displacements based on the optimal motion parameters M and T. Then strains and/or rotations are estimated by taking partial derivatives of the estimated displacements.

Initialization component 302 initializes the motion parameter(s) 304a, 304b. System 300 iterates through a series of candidate motion parameters by warping first image 202 to the first warped image 206 by the image warping component 102, inputting the warped first image 206 and the second image into the estimation component 104. A compensation of speckle pattern variations is achieved through the estimation component 104 using each candidate of motion parameters, and some criteria are used to decide whether the compensation is optimal by the optimization component 306. If the current candidate achieves an optimal compensation, the optimal motion parameters will be exported as the optimal motion parameter 310.

The optimization component 306 can use quantitative measures to decide whether an optimal compensation is present. For example, the compensation of speckle pattern variations is optimal if the patterns are the most similar to each other. Matching metrics, such as sum of absolute difference (SAD), sum of square difference (SSD) and/or correlation coefficient (CC), can be used in both the search of matched patterns and the evaluation of pattern similarity.

The search for the optimal motion parameter(s) 310 can be achieved by the optimization component 310 by enumerating all possible candidates of motion parameters under additional constraints (e.g., a tissue incompressibility constraint, a contraction of the search space, a time threshold or computation threshold, such as time limit or processing cycle limit) with/without a multi-scale framework. Moreover, the candidate set of motion parameters can be decided online under the guidance of appropriate heuristics (e.g., gradient based methods, greedy methods, forcing a preference to some subset of candidates) with/without a multi-scale framework.

System 300 achieves the goal of the affine warping method by to producing a robust and accurate estimation of tissue motion, even when tissue motion is large. For example, the optimal motion parameter(s) 310 is estimated correctly and exported to describe the tissue motion. Estimation of strains and rotations is then generated directly or indirectly from the optimal motion parameter(s) 310.

It can be shown that the affine warping method employed by system 300 is able to achieve similar estimation accuracy as the coupled filtering method, even when tissue motion is large. Since the affine warping method employed by system 300 does not involve the convolution of the point spread function (PSF) of the ultrasound system as in the coupled filtering method, it is less time consuming than the coupled filtering method. Also, the affine warping method does not assume a known, invariant point spread function (PSF) and can be applied to both B mode (BM) and radio frequency (RF) ultrasound images, while coupled filtering method can only be applied to RF images.

Figure 4:
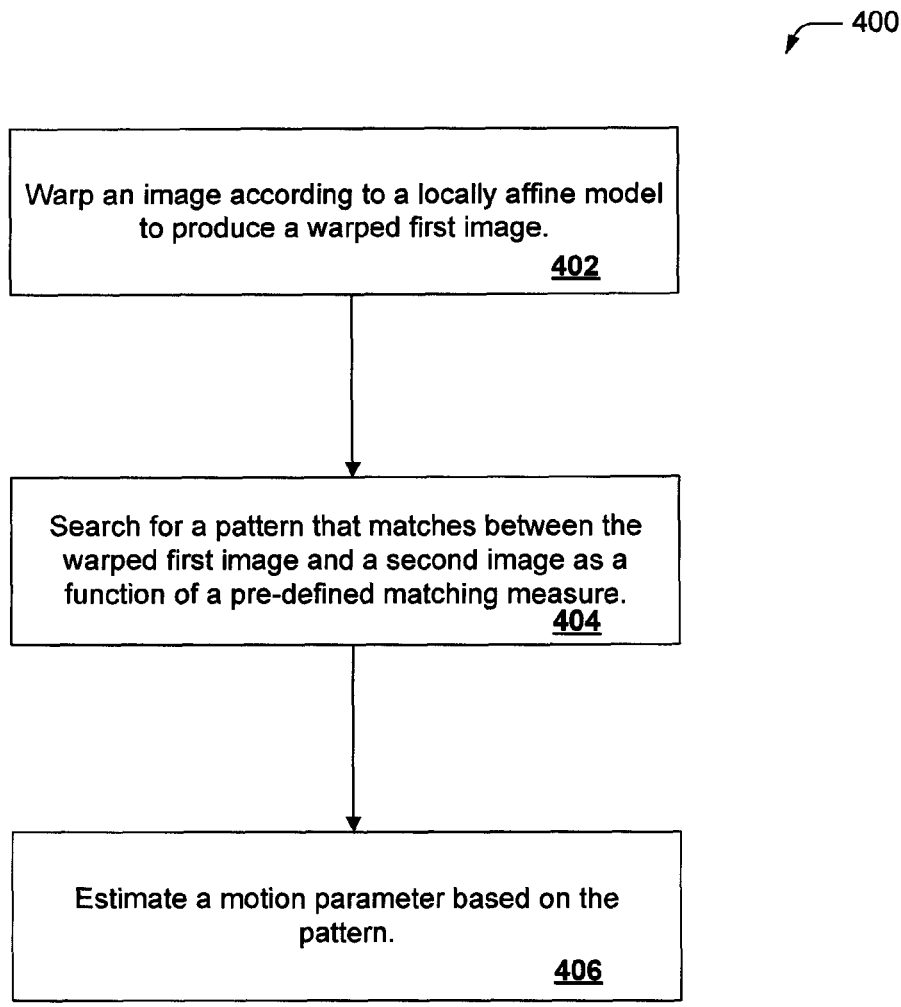
FIG. 4 is an example non-limiting process flow diagram of a method that facilitates image analysis with compensation of feature motion decorrelation, according to an embodiment of the disclosure.
Figure 5:
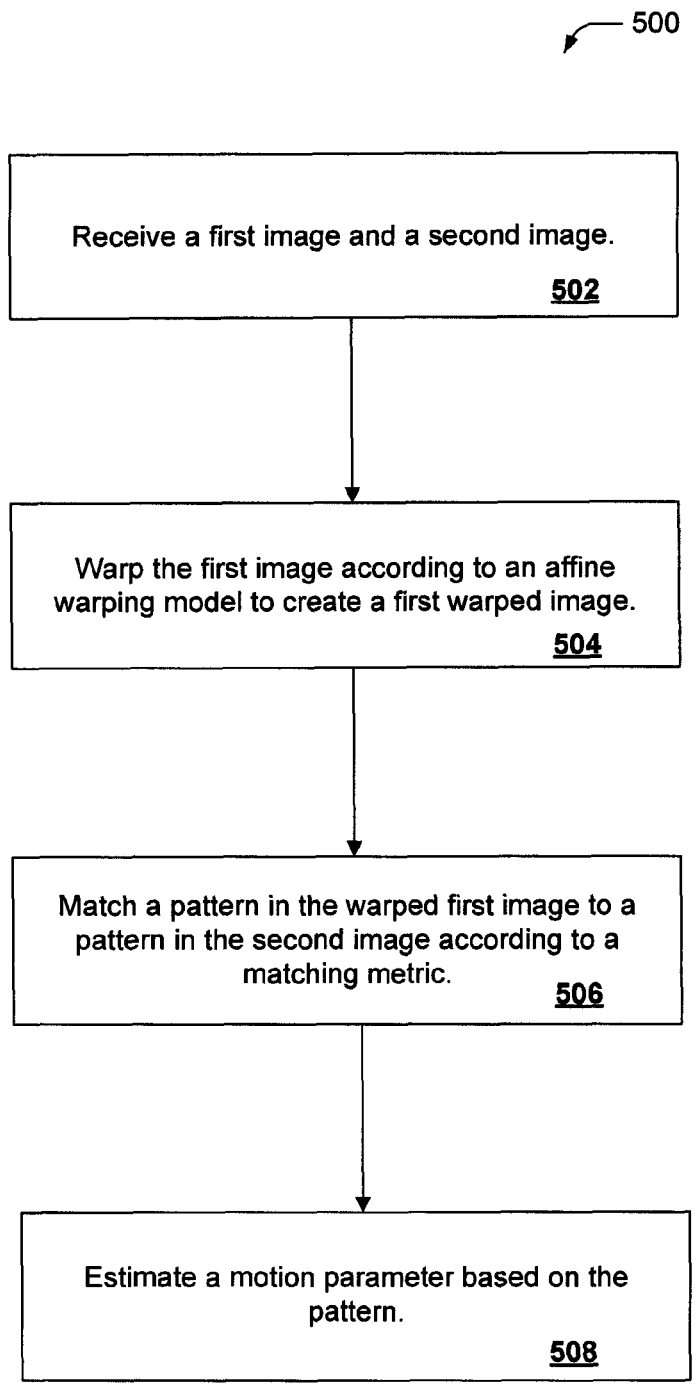
FIG. 5 is an example non-limiting process flow diagram of a method that facilitates compensation of feature motion decorrelation, according to an embodiment of the disclosure.
Figure 6:
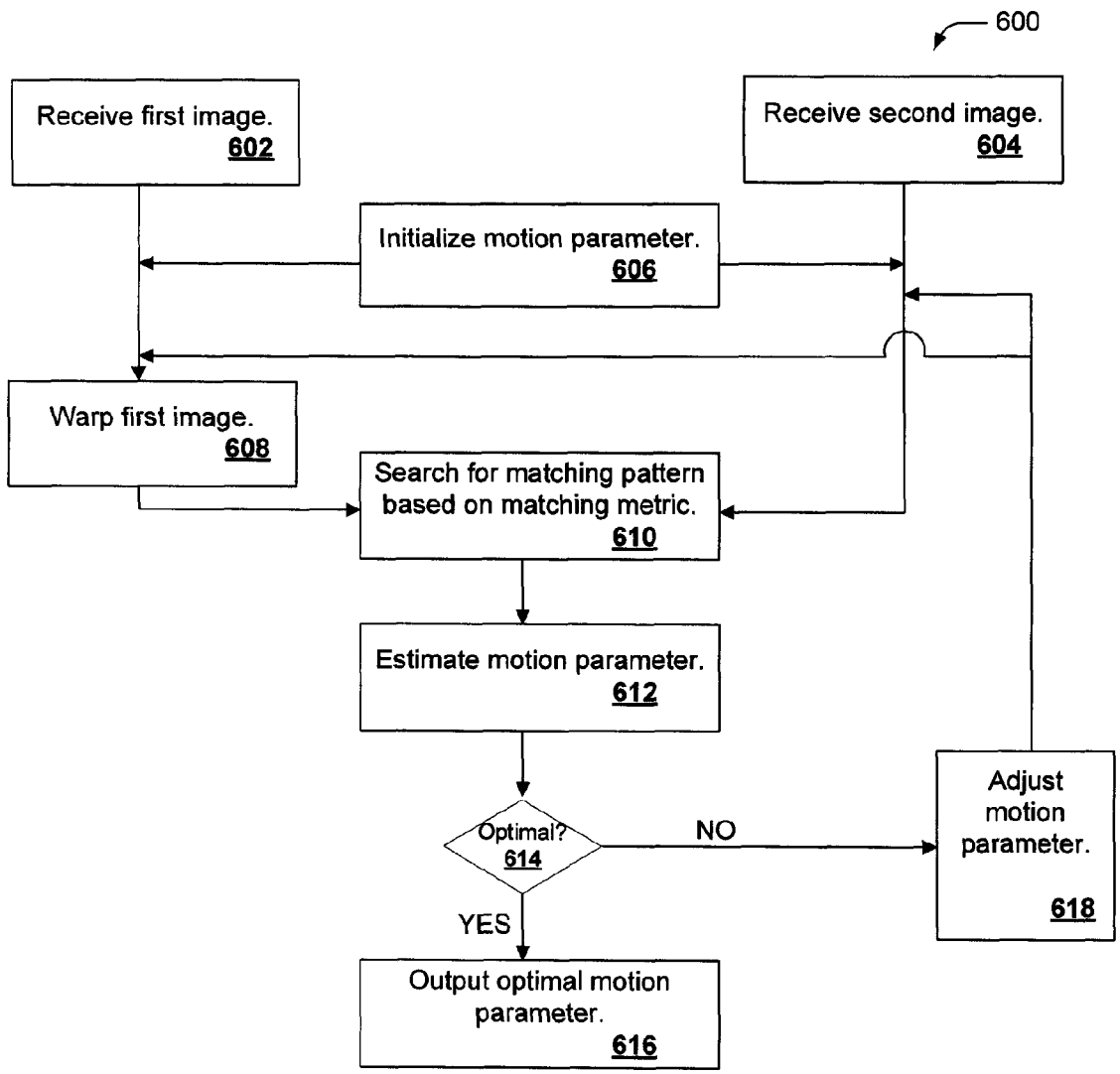
FIG. 6 is an example non-limiting process flow diagram of a method that optimizes a motion parameter to facilitate compensation of feature motion decorrelation, according to an embodiment of the disclosure.

FIGS. 4-6 illustrate methods and/or flow diagrams in accordance with embodiments of this disclosure. For simplicity of explanation, the methods are depicted and described as a series of acts that can be performed by a system including a processor. However, acts in accordance with this disclosure can occur in various orders and/or concurrently, and with other acts not presented and described in this disclosure. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be further appreciated that the methods disclosed in this specification are capable of being stored on an article of manufacture to facilitate transporting and transferring such methods to hardware devices.

Referring now to FIG. 4, illustrated is an example non-limiting process flow diagram of a method 400 that facilitates image analysis with compensation of feature motion decorrelation, according to an embodiment of the disclosure. The method 400 is an affine warping method. At element 402, an image is warped according to a locally affine model to produce a warped first image. At element 404, for a match between the warped first image and a second image is searched for and discovered as a function of a pre-defined matching measure and estimating, by the system, a motion parameter based on the match. At element 406, a motion parameter is estimated based on the match.

Referring now to FIG. 5, illustrated is an example non-limiting process flow diagram of a method 500 that facilitates compensation of feature motion decorrelation, according to an embodiment of the disclosure. The method 500 is an affine warping method. At element 502, a first image or set of images and a second image or set of images are received. At element 504, the first image is warped according to an affine warping model to create a first warped image. At element 506, a match between the warped first image and the second image according to a matching metric. At element 508, a motion parameter is estimated based on the match.

Referring now to FIG. 6, illustrated is an example non-limiting process flow diagram of a method 600 that optimizes a motion parameter to facilitate compensation of feature motion decorrelation, according to an embodiment of the disclosure. The method 600 is an affine warping method. At element 602, a first image is received. At element 604, a second image is received. At element 606, a motion parameter is initialized. At element 606, the first image is warped to a first warped image. Based on the first warped image and the second image, at element 610, a matching pattern between the first warped image and the second image is searched for based on a matching metric. At element 612, a motion parameter is estimated based on the match. At element 614, it is determined whether the motion parameter is optimal. At element 616, if the motion parameter is optimal, the motion parameter is output to facilitate determination of motion and/or mechanical properties of an imaged object. At 618, if the motion parameter is not optimal, the motion parameter is adjusted and acts 608-614 are repeated with an input of the adjusted motion parameter.

FIGS. 7-36 illustrate the feasibility of the affine warping method compared to the coupled filtering method. The affine warping method is able to achieve reliable strain estimations as the coupled filtering method even though it cannot achieve strictly identical speckle patterns. It is also able to handle extremely difficult cases and it is computationally not as intensive as the coupled filtering method. The affine warping method is able to work on B mode images, while the coupled filtering method is restricted to RF images. The experimental results of FIGS. 7-36 show that the affine warping method provides similarly good performance as the coupled filtering method in compensating for feature motion decorrelation, even when tissue deformation is very large.

Figure 7:
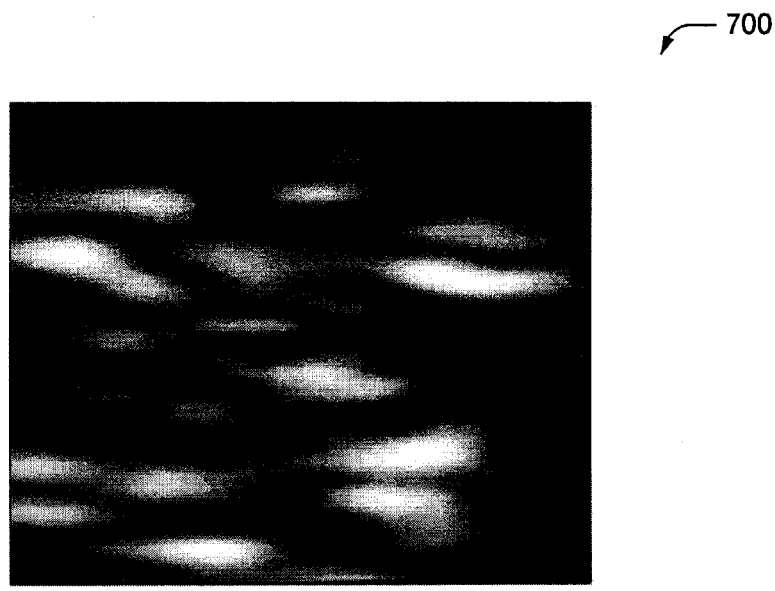
FIG. 7 is an example non-limiting input image from a three dimensional ultrasound study, according to an embodiment of the disclosure.

Referring now to FIG. 7, illustrated is an example non-limiting input image 700 from a three dimensional ultrasound study, according to an embodiment of the disclosure. Three dimensional simulation data are used to demonstrate the results of the affine warping method and to compare the results of the affine warping method to the coupled filtering method.

The three dimensional ultrasound images were generated by the Field II program, a widely accepted ultrasound image simulation tool. The transducer frequency was set as 3 MHz and the fractional bandwidth of transducer was set as 0.5. In the three dimensional simulation, a multi-row linear array of 16×16 transducer elements without kerf was used. Dynamic focusing was used to achieve a high resolution at different depths. FIG. 7 shows one slice of a simulated three dimensional ultrasound image.

Generally, in a three dimensional simulation, 2,000 tissue scatterers are uniformly distributed in a 10 mm×10 mm×10 mm region of interest. The size of resolution cell (e.g., the full width half maximum of the PSF) is approximately 0.6 mm×1.8 mm×1.8 mm. There are on average about 4 tissue scatterers in each resolution cell. The associated reflectance coefficients of tissue scatterers follow a Gaussian distribution and are bounded between 0 and 1. The sampling rates along the axial, lateral and elevational direction are 20 pixels/mm, 10 pixels/mm and 10 pixels/mm, respectively. The size of the three dimensional ultrasound images is 201×101×101 voxels.

After constructing the first ultrasound image volume as the reference, the motion of tissue scatterrers were simulated according to:

$$x_n = MX_n + T.$$

The Field II program was used again to construct the second ultrasound image volume. Three types of three dimensional affine motion were simulated, including lateral compression expansion (i.e., compression expansion primarily along the lateral direction), shearing along the axial-lateral plane (i.e., the elastic axis is perpendicular to the beam direction) and lateral rotation (i.e., the rotation axis is perpendicular to the beam direction). The three cases are chosen because speckle pattern variations are the largest, while more types of locally affine motion yield similar results and are not discussed here. In all three cases, the translation vector T is zero, assuming the center of the region of interest (ROI) locates at the origin. The M matrix for the three types of three dimensional affine motion is shown as follows:

Lateral Compression Expansion $$M = \begin{bmatrix} 1+0.5\varepsilon & & \\ & 1-\varepsilon & \\ & & 1+0.5\varepsilon \end{bmatrix};$$

Shearing Along the Axial-Lateral Plane $$M = \begin{bmatrix} 1 & \varepsilon & \\ \varepsilon & 1 & \\ & & 1 \end{bmatrix};$$

Lateral Rotation $$M = \begin{bmatrix} 1 & \theta & \\ & 1 & \\ -\theta & & 1 \end{bmatrix}.$$

Figure 8:
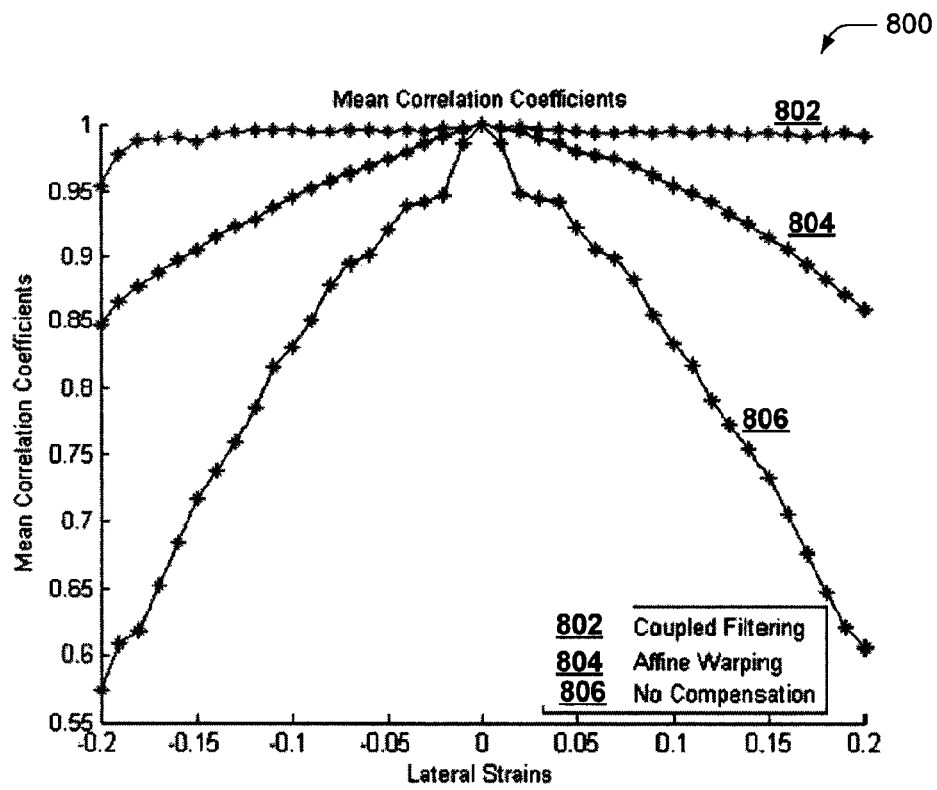
FIGS. 8-10 are example non-limiting graphs of mean correlation coefficients of image patterns with respect to motion in the three dimensional ultrasound study, according to an embodiment of the disclosure.
Figure 9:
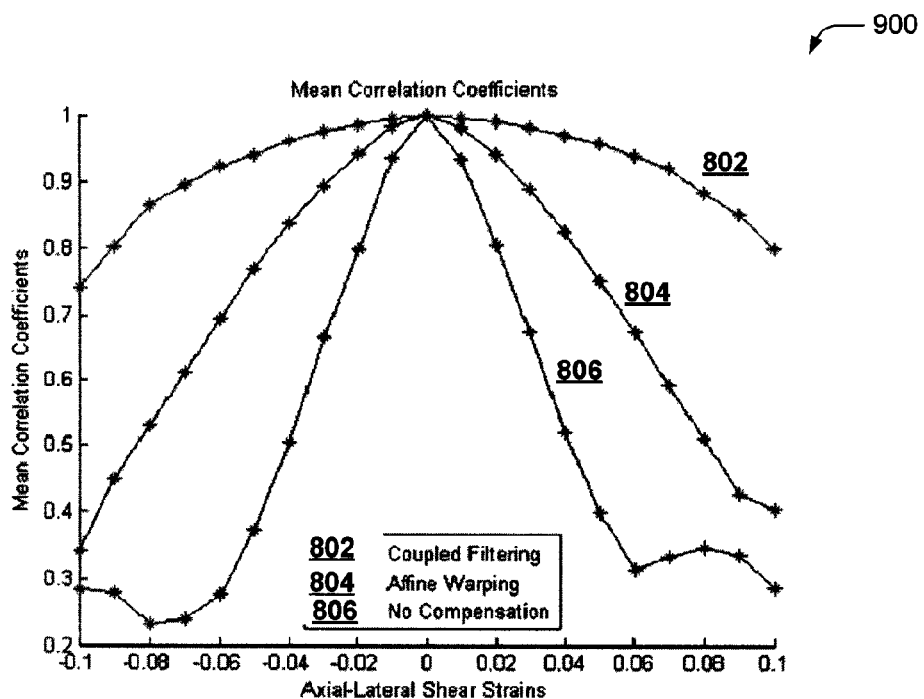
Figure 10:
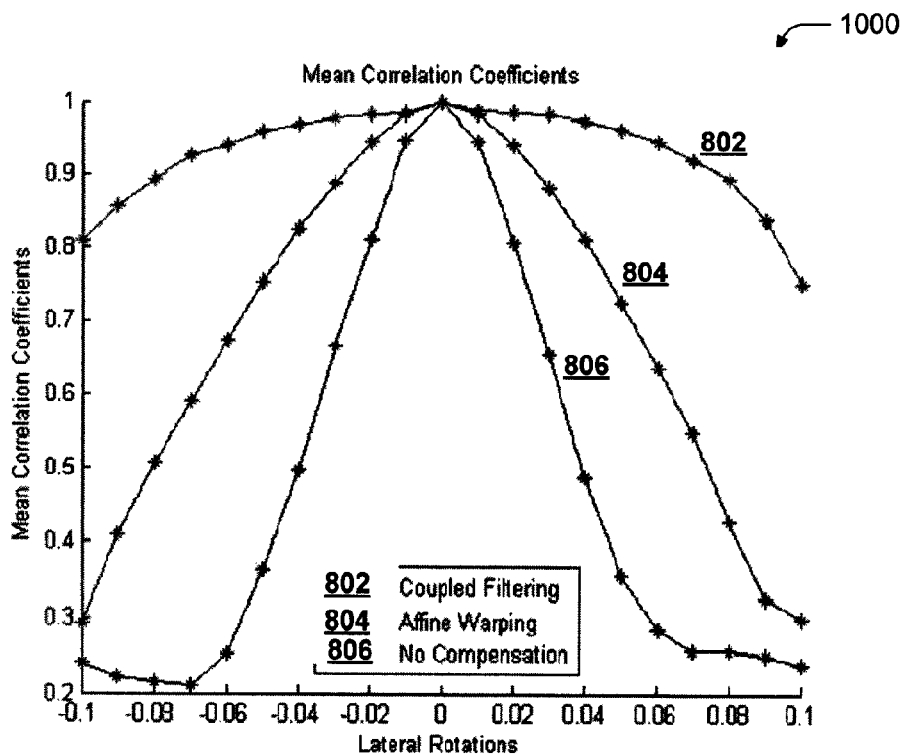

Referring now to FIGS. 8-10, illustrated are example non-limiting graphs of mean correlation coefficients of matched patterns with respect to motion in the three dimensional ultrasound study, according to an embodiment of the disclosure. FIG. 8 illustrates mean correlation coefficients for the case of lateral compression/expansion. FIG. 9 illustrates mean correlation coefficients for the case of shearing along the axial-lateral plane. FIG. 10 illustrates mean correlation coefficients for the case of lateral rotation. In all three cases, affine warping 804 is compared to coupled filtering 802 and no compensation 806.

A window containing 25 ×37 ×37 voxels was used to search for a matched pattern in the other image volume. Correlation coefficient (CC) was used as the matching metric and the mean of correlation coefficients for each window was calculated. A total of 9 ×9×9 =729 windows were used.

For the compression/expansion case (FIG. 8), the applied normal strain varies from −20% to 20% with a step of 1%. For the shearing case (FIG. 9), the applied shear strain varies from −10% to 10% with a step of 1%. For the rotation case (FIG. 10), the applied rotation angle varies from −0.1 rad to 0.1 rad with a step of 0.01 rad. All the three cases included extremely large motion situations.

In the cases of lateral compression expansion, mean correlation coefficients remain close to one for the coupled filtering method 802, showing that the coupled filtering method is able to recover identical speckle patterns. In some extreme cases (e.g., applied normal strains larger than 15%), the mean correlation coefficients start to drop. While in the cases of shearing along axial-lateral plane and lateral rotation, mean correlation coefficients drop gradually for the coupled filtering method 802. This is because the PSF of ultrasound system does not remain the same at different spatial positions. Thus additional speckle pattern variations are available due to the variance in the PSF. The mean correlation coefficients drop gradually for the affine warping method 804, since speckle pattern variations due to the interference nature of ultrasound images are not compensated. The mean correlation coefficients drop dramatically without compensation of feature motion decorrelation 806.

Figure 11:
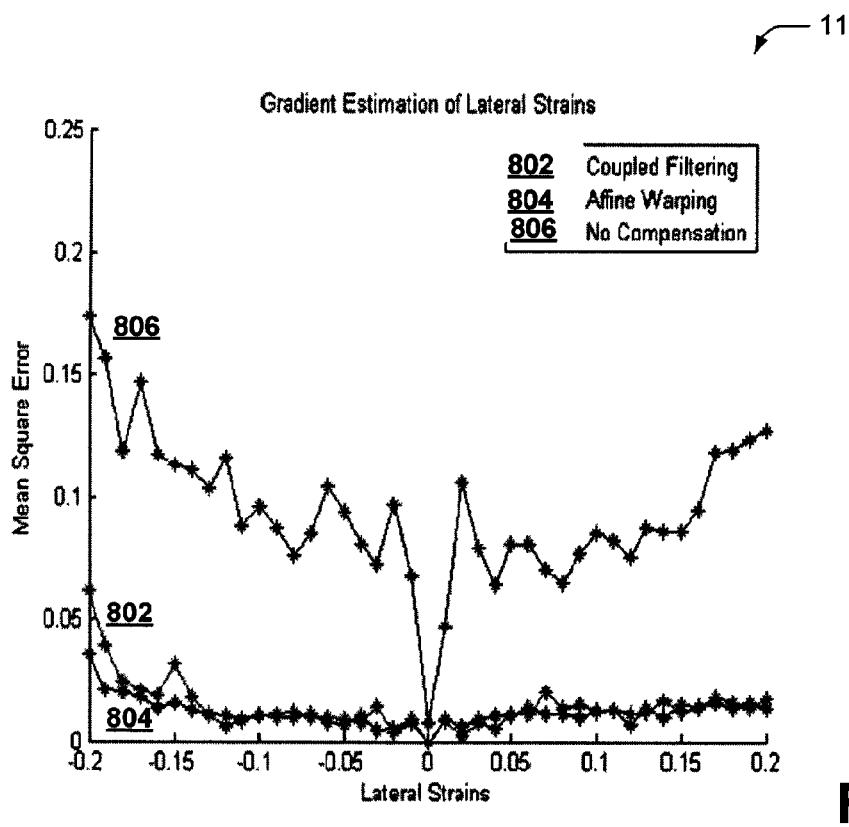
FIGS. 11-13 are example non-limiting graphs of mean square errors with respect to motion in the three dimensional ultrasound study, according to an embodiment of the disclosure.
Figure 12:
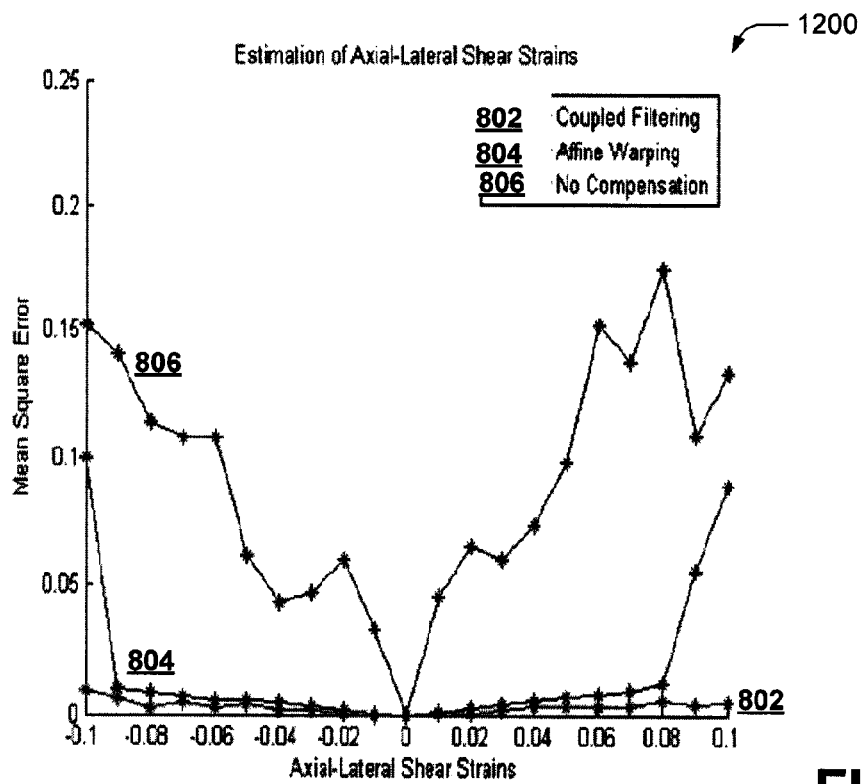
Figure 13:
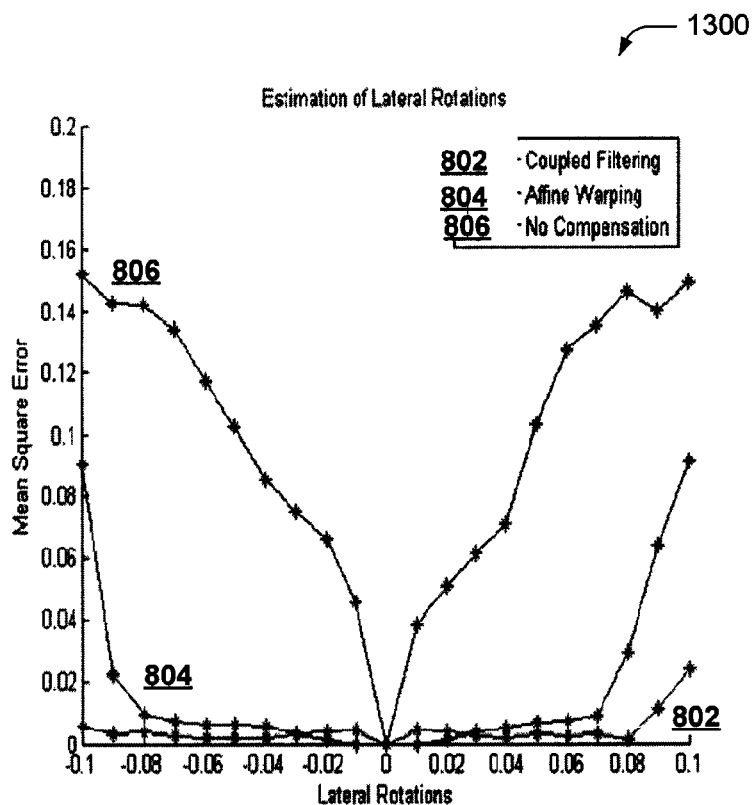

Referring now to FIGS. 11-13, illustrated are example non-limiting graphs of mean square errors of motion deformation estimates with respect to motion in the three dimensional ultrasound study, according to an embodiment of the disclosure. FIG. 11 illustrates mean square errors for the case of lateral compression/expansion. FIG. 12 illustrates mean square errors for the case of shearing along the axial-lateral plane. FIG. 13 illustrates gradient estimation of mean square errors for the case of lateral rotation. In all three cases, affine warping 804 is compared to coupled filtering 802 and no compensation 806.

Mean square errors were calculated as the mean squared differences between the estimated motion parameters and the underlying true motion parameters. A window of the size 25×37×37 was used to search for a matched pattern in the other image volume, while the mean square error of motion estimation for all windows was calculated. A total of 9×9× 9=729 windows were used.

For the compression/expansion case (FIG. 11), the applied normal strain varies from −20% to 20% with a step of 1%. For the shearing case (FIG. 12), the applied shear strain varies from −10% to 10% with a step of 1%. For the rotation case (FIG. 13), the applied rotation angle varies from −0.1 rad to 0.1 rad with a step of 0.01 rad. All the three cases include extremely large motion situations.

In all three cases, mean square errors are relatively small for both the coupled filtering method and the affine warping method, except some extreme cases (e.g., applied normal strains larger than 15% for the case of lateral compression/expansion, applied shear strain larger than 8% for the case of shearing along axial-lateral plane and the applied rotation angle larger than 0.07 rad for the case of lateral rotation), where even the coupled filtering method may fail. Note that the zig-zag structure is due to the nature of discrete optimization and discrete input image volumes. Direct tissue motion estimation fails if feature motion decorrelation is not compensated.

Figure 14:
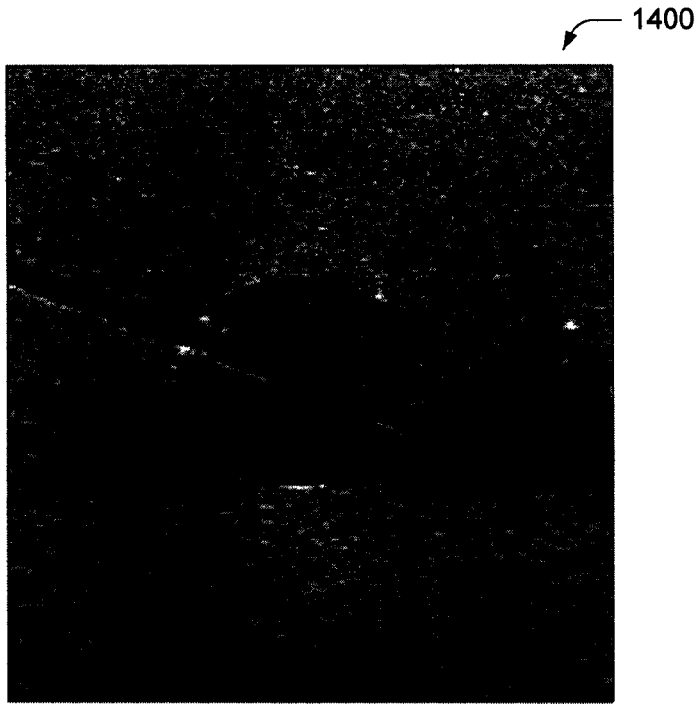
FIG. 14 is an example non-limiting input image of a two dimensional tissue mimicking gelatin phantom, according to an embodiment of the disclosure.

Referring now to FIG. 14, illustrated is an example non-limiting input image of a two dimensional tissue mimicking gelatin phantom, according to an embodiment of the disclosure. Two dimensional phantom data experiments are also used to demonstrate the results of the affine warping method. A tissue mimicking gelatin phantom was compressed down with a controlled machine. A cylindrical region which is about 6 times stiffer than other parts was included to mimic a breast lesion. In addition, a channel filled with liquids was placed in the phantom to mimic a blood vessel, which would have the highest strain when compressed.

A 2 percent and 5 percent compression of the phantom were performed while ultrasound images before and after the compressions were recorded. The performance of the affine warping method was compared with the coupled filtering method as well as the companding method.

Figure 15:
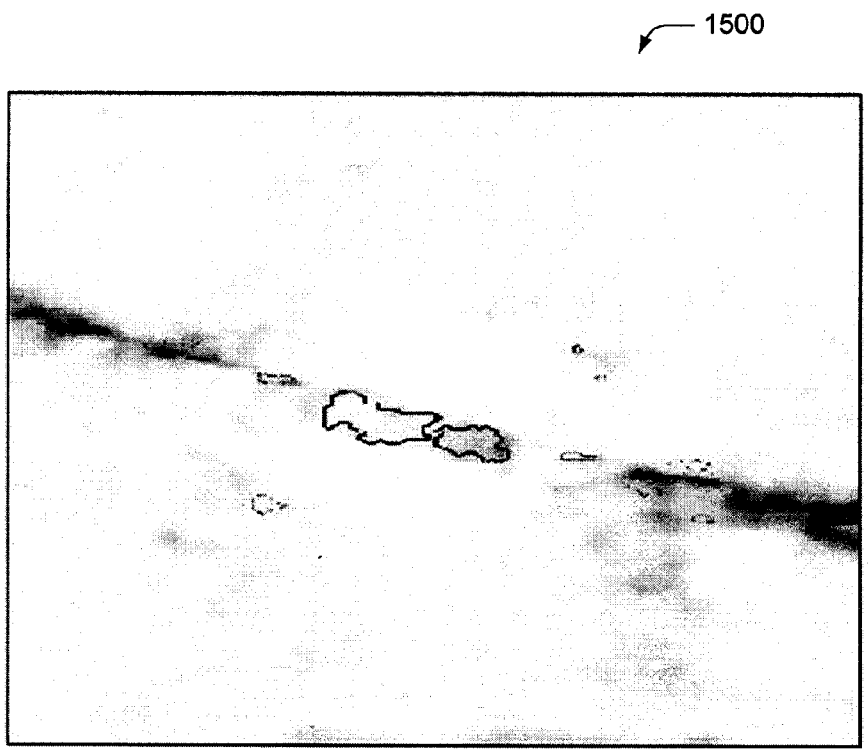
FIG. 15 is an example non-limiting correlation coefficient for the coupled filtering method under 2% compression of the two dimensional tissue mimicking gelatin phantom, according to an embodiment of the disclosure.
Figure 16:
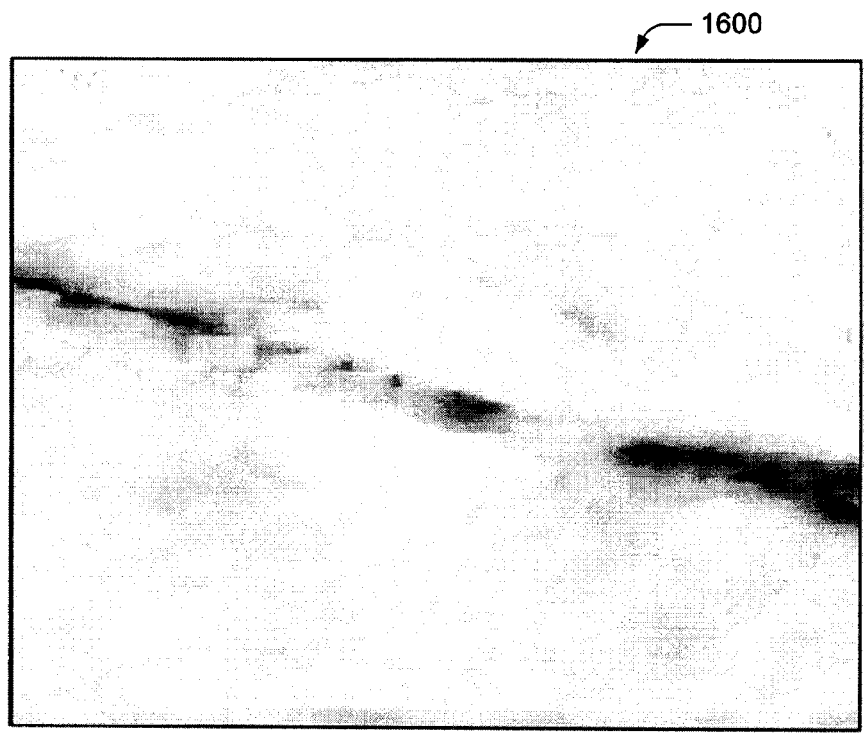
FIG. 16 is an example non-limiting correlation coefficient for the affine warping method under 2% compression of the two dimensional tissue mimicking gelatin phantom, according to an embodiment of the disclosure.
Figure 17:
FIG. 17 is an example non-limiting correlation coefficient for the companding method under 2% compression of the two dimensional tissue mimicking gelatin phantom, according to an embodiment of the disclosure.

FIGS. 15-17 illustrate exemplary correlation coefficients for the coupled filtering method (FIG. 15), the affine warping method (FIG. 16) and the companding method (FIG. 17) in the 2 percent compression case. A window containing 113× 31 pixels was used to search for a matched pattern in the other image and correlation coefficient was chosen as the matching metric. A total of 385×257=98945 windows were used, and the correlation coefficient for each window was calculated and displayed. In the 2 percent case, tissue deformation and speckle pattern variations are not large.

For all the three methods, mean correlation coefficients above 0.9 were achieved, which demonstrate that most of speckle pattern variations have been compensated. The mean correlation coefficients for the coupled filtering method, the affine warping method and the companding method are 0.96, 0.95 and 0.92, respectively. The coupled filtering method and the affine warping method are able to reduce more speckle pattern variations than the companding method. The performance of the affine warping method is similar to the coupled filtering method.

For all the three methods, correlation coefficients drop dramatically in the channel region. This is because tissue motion in the region of channel is different from the region of gelatin, and the local area used in the three methods is not small enough so that the estimation of tissue motion in the channel region is corrupted by different kinds of tissue motion. A smaller correlation window size will improve the estimation around the channel region, but estimation accuracy in the gelatin region will be sacrificed since speckle patterns will not be enough for robust tracking.

Figure 18:
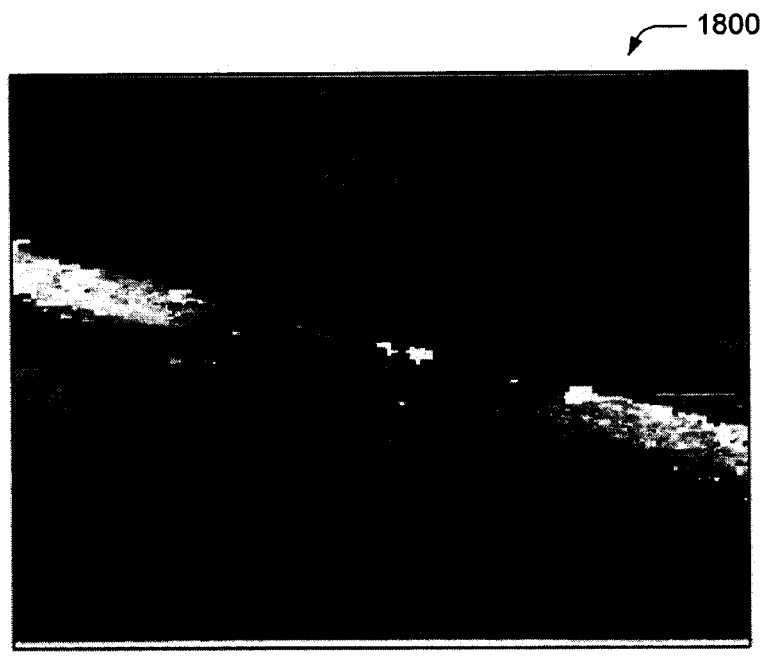
FIG. 18 is an example non-limiting axial strain estimation for the coupled filtering method under 2% compression of the two dimensional tissue mimicking gelatin phantom, according to an embodiment of the disclosure.
Figure 19:
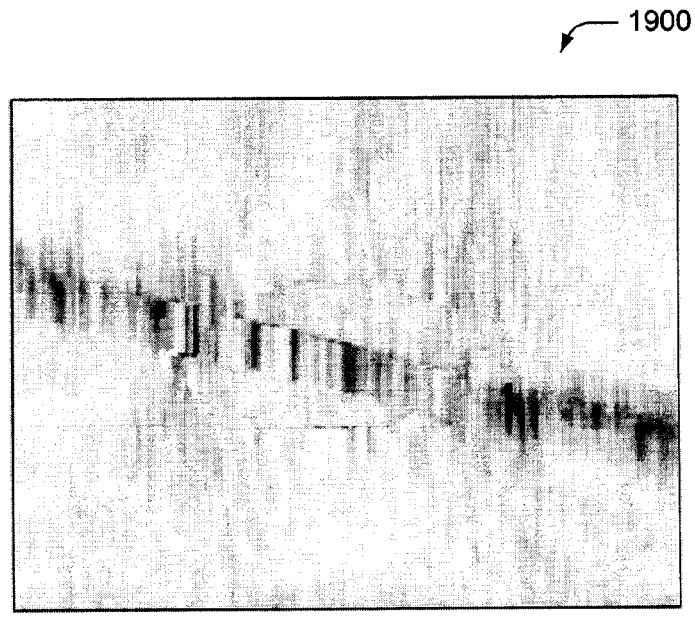
FIG. 19 is an example non-limiting axial strain estimation for the affine warping method under 2% compression of the two dimensional tissue mimicking gelatin phantom, according to an embodiment of the disclosure.
Figure 20:
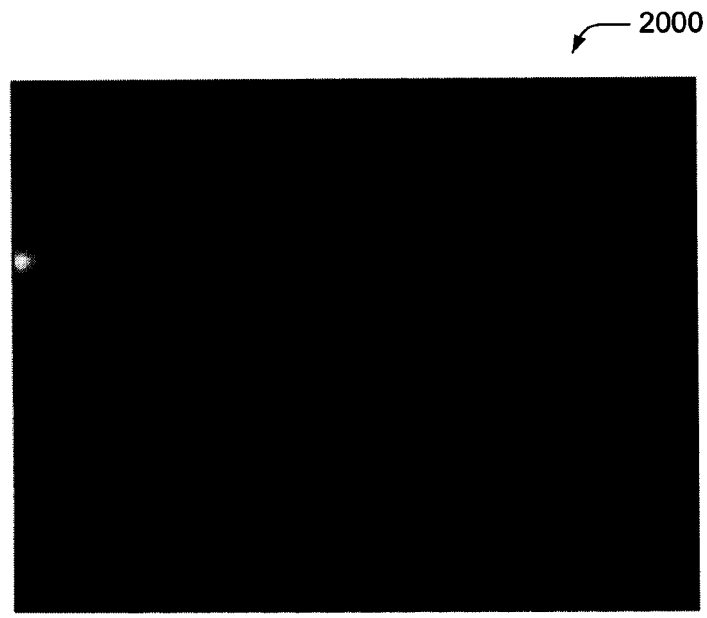
FIG. 20 is an example non-limiting axial strain estimation for the companding method under 2% compression of the two dimensional tissue mimicking gelatin phantom, according to an embodiment of the disclosure.

FIGS. 18-20 illustrate example axial strain estimations for the coupled filtering method (FIG. 18), the affine warping method (FIG. 19) and the companding method (FIG. 20) in the 2 percent compression case. A window containing 113× 31 pixels was used to search for a matched pattern in the other image and the estimated axial strains for each window was displayed. A total of 385×257=98945 windows were used. In the 2 percent case, since speckle pattern variations are not large, robust estimation of tissue motion is not very difficult.

For all the three methods, low axial strains were detected in the hard inclusion region, showing that all the three methods are able to distinguish tissue regions with different stiffness. Only part of the channel region was revealed by the coupled filtering method and the affine warping method, while the channel region revealed by the companding method is much thicker than the true region. This is mainly because the local area used in the three methods is not small enough so that the estimation of tissue motion in the channel region is corrupted by different tissue motion in other regions. Axial strain estimations in the gelatin region for the coupled filtering method and the affine warping method are not as smooth as the companding method, mainly because a tissue incompressibility constraint is used in the two methods, limiting the estimation accuracy of axial strains for the sake of more accurate lateral strain estimations.

Figure 21:
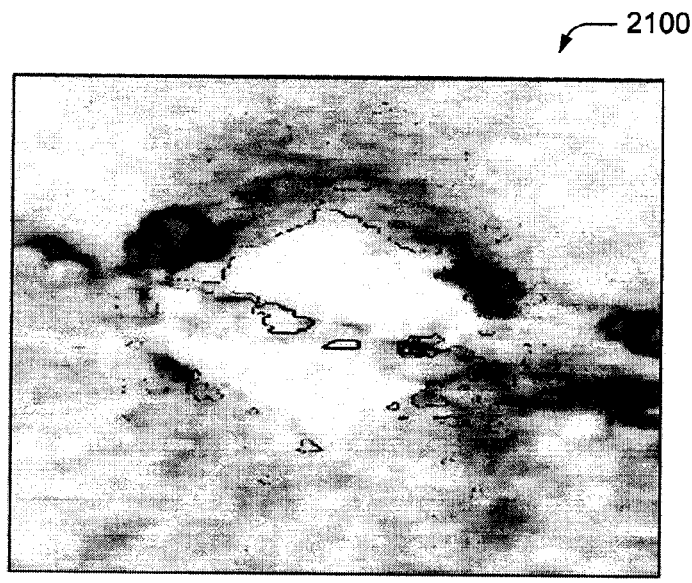
FIG. 21 is an example non-limiting correlation coefficient for the coupled filtering method under 5% compression of the two dimensional tissue mimicking gelatin phantom, according to an embodiment of the disclosure.
Figure 22:
FIG. 22 is an example non-limiting correlation coefficient for the affine warping method under 5% compression of the two dimensional tissue mimicking gelatin phantom, according to an embodiment of the disclosure.
Figure 23:
FIG. 23 is an example non-limiting correlation coefficient for the companding method under 5% compression of the two dimensional tissue mimicking gelatin phantom, according to an embodiment of the disclosure.

FIGS. 21-23 illustrate exemplary mean correlation coefficients for the coupled filtering method (FIG. 23), the affine warping method (FIG. 24) and the companding method (FIG. 25) in the 5 percent compression case. A window containing 113×31 pixels was used to search for a matched pattern in the other image and correlation coefficient was chosen as the matching metric. A total of 385×257=98945 windows were used and the correlation coefficient for each window was calculated and displayed. In the 5 percent case, tissue deformation as well as speckle pattern variations are large, which are usually considered to be difficult.

The mean correlation coefficients for the coupled filtering method and the affine warping method are 0.87 and 0.83, respectively, while the mean correlation coefficient for the companding method is 0.65. Such a significant drop of correlation coefficients indicates that the companding method is not enough to compensate for image variations in this large deformation case.

For the coupled filtering method and the affine warping method, correlation coefficients drop dramatically in the channel region. Correlation coefficients around the hard inclusion region also drop. This is because tissue motion in different regions is different, and the local area used in the two methods is not small enough so that the estimation of tissue motion in one region is corrupted by different tissue motion in other regions.

Figure 24:
FIG. 24 is an example non-limiting axial strain estimation for the coupled filtering method under 5% compression of the two dimensional tissue mimicking gelatin phantom, according to an embodiment of the disclosure.
Figure 25:
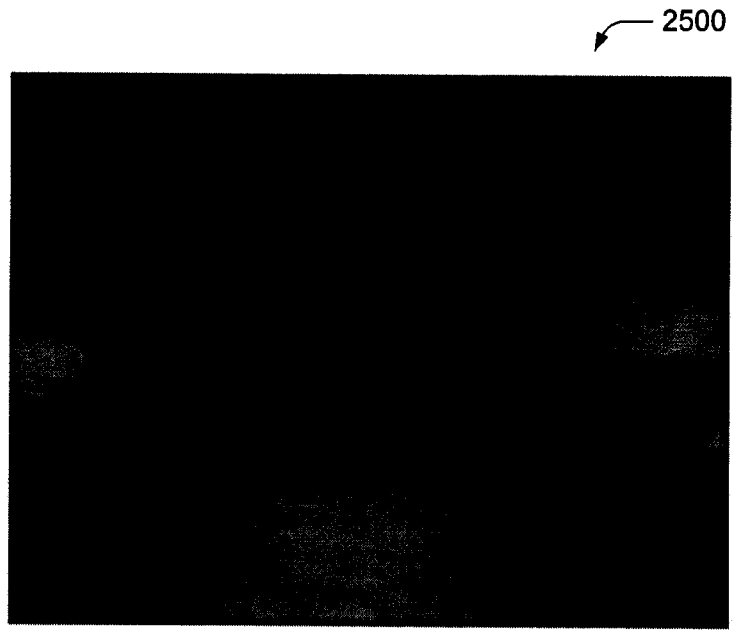
FIG. 25 is an example non-limiting axial strain estimation for the affine warping method under 5% compression of the two dimensional tissue mimicking gelatin phantom, according to an embodiment of the disclosure.
Figure 26:
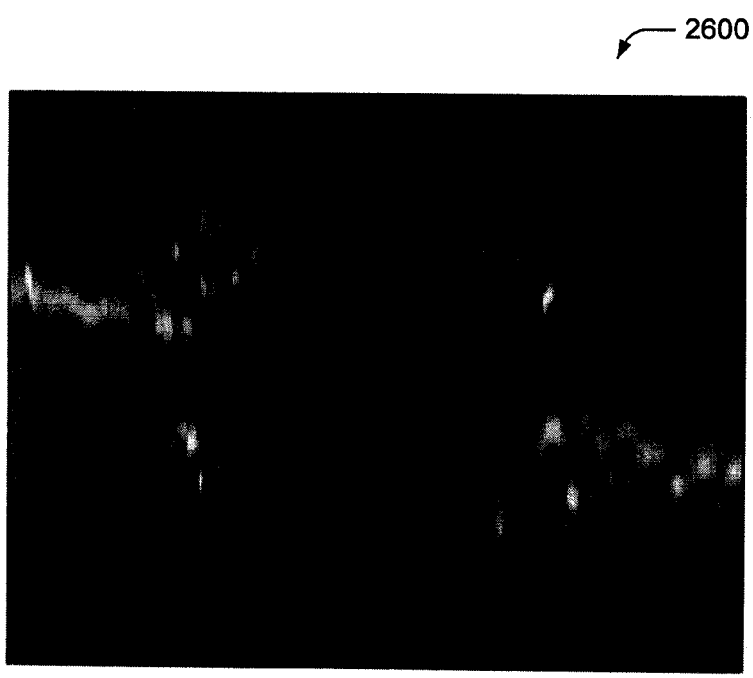
FIG. 26 is an example non-limiting axial strain estimation for the companding method under 5% compression of the two dimensional tissue mimicking gelatin phantom, according to an embodiment of the disclosure.

Referring now to FIGS. 24-26, illustrated are exemplary axial strain estimations for the coupled filtering method (FIG. 24), the affine warping method (FIG. 25) and the companding method (FIG. 26) in the 5 percent compression case. A window containing 113×31 pixels was used to search for a matched pattern in the other images and the estimated axial strains for each window was displayed. A total of 385×257=98945 windows were used. In the 5 percent case, speckle pattern variations are large, which is considered to be difficult.

The companding method fails to produce reliable estimation of axial strains since speckle pattern variations are not adequately compensated. For the coupled filtering method and the affine warping method, low axial strains are detected in the hard inclusion region, showing that both methods are able to distinguish tissue regions with different stiffness, even in extremely difficult cases. Only part of the channel region is revealed by the coupled filtering method and the affine warping method. Small deviation of axial strain estimation is also observed around the hard cylinder region. This is mainly because the local area used in both methods is not small enough so that the estimation of tissue motion in the channel region is corrupted by different tissue motion in other regions. Axial strain estimations in the gelatin region for the coupled filtering method and the affine warping method are not smooth enough, mainly because a tissue incompressibility constraint is used in both methods, limiting the estimation accuracy of axial strains for the sake of more accurate lateral strain estimations.

Moreover, both three dimensional simulations and two-dimensional phantom data experiments are also used to demonstrate the application of the affine warping method on B mode ultrasound images. Identical settings are adopted in simulations and phantom data experiments, and the performance of speckle tracking methods using B mode and RF ultrasound images, respectively, is compared.

In three dimensional simulation, a comparative study on the affine warping method using RF images, the affine warping method using B mode images, the direct correlation method using RF images and the direct correlation method using B mode images is conducted. The performance of the affine warping method using RF images, the affine warping method using B mode images, the direct correlation method using RF images and the direct correlation method using B mode images is compared under three cases of three dimensional tissue motion, lateral compression/expansion, shearing along the axial-lateral plane and lateral rotation, respectively. All the three cases include extremely large motion situations.

Figure 27:
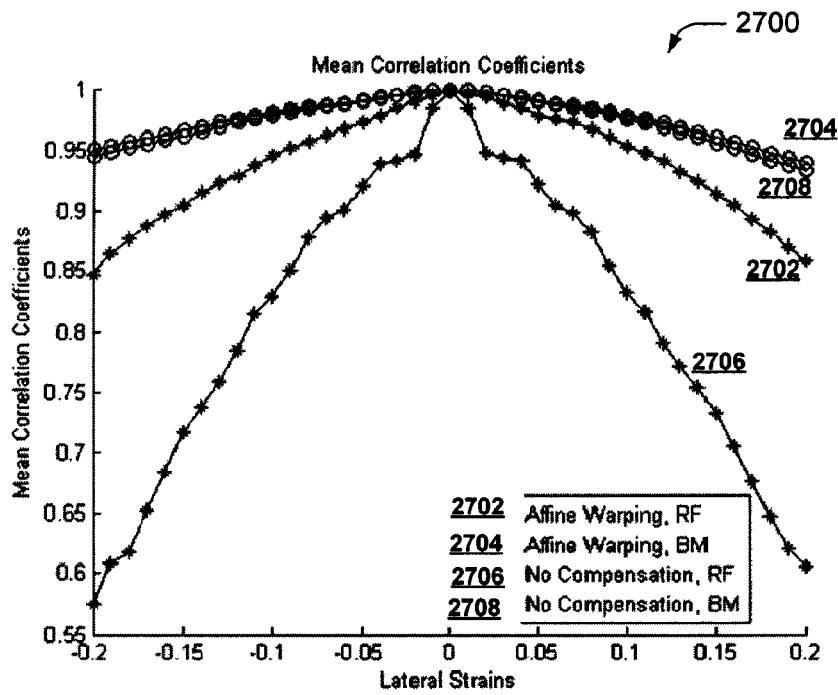
FIGS. 27-29 are example non-limiting graphs of mean correlation coefficients of image patterns with respect to motion in a three dimensional ultrasound simulation study, according to an embodiment of the disclosure.
Figure 28:
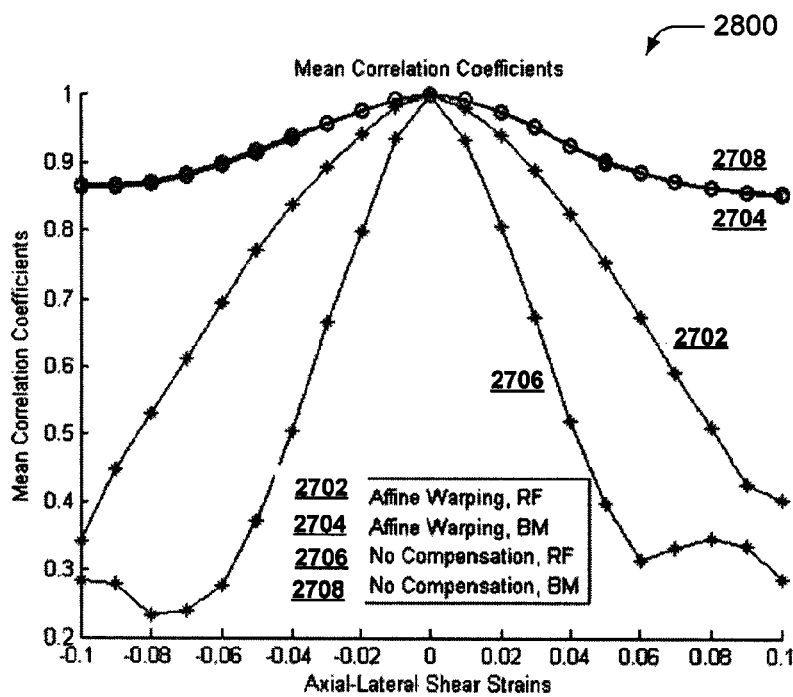
Figure 29:
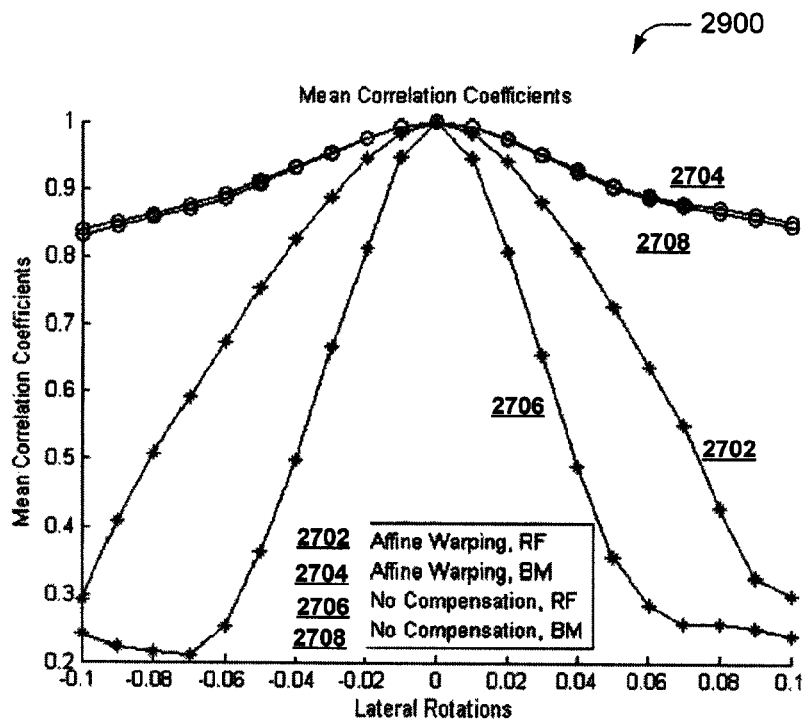

Referring now to FIGS. 27-29, illustrated are example non-limiting graphs of mean correlation coefficients of matched patterns with respect to motion in a three dimensional ultrasound simulation study, according to an embodiment of the disclosure. FIG. 27 corresponds to lateral compression/expansion; FIG. 28 corresponds to shearing along the axial-lateral plane; and FIG. 29 corresponds to lateral rotation. Affine warping RF is shown at element 2702, affine warping B mode is shown at element 2704, no compensation RF is shown at element 2706, and no compensation B mode is shown at 2708.

In all three cases, much higher mean correlation coefficients are achieved by the two methods using B mode images, partially because phase information has been discarded in B mode images. When tissues undergo complex motion, the phase information in RF images changes a lot, which leads to a dramatic drop of correlation coefficients when matching. In conclusion, speckle pattern variations are much smaller in B mode images than in RF images.

Figure 30:
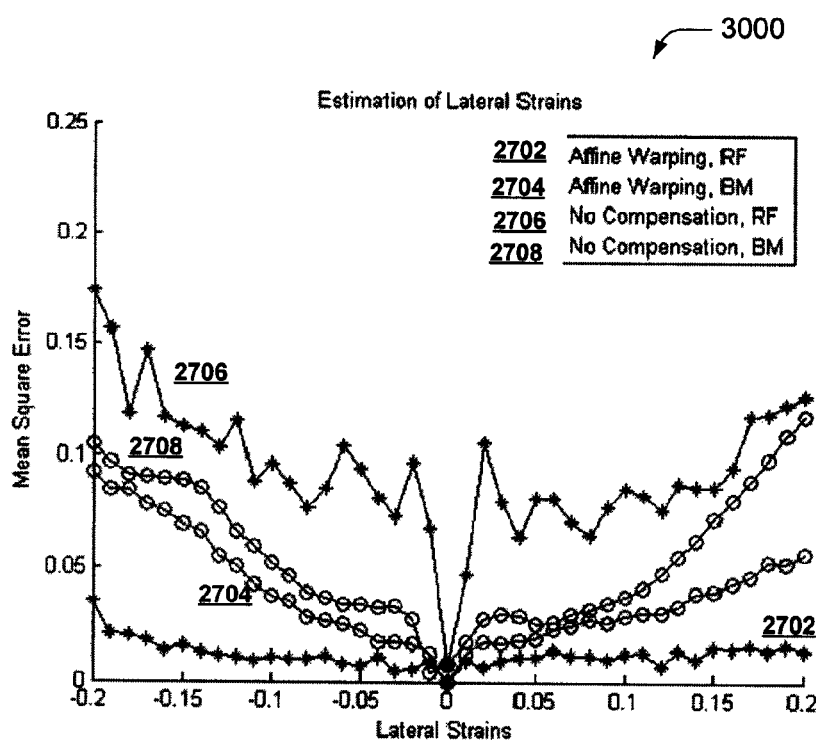
FIG. 30 is an example non-limiting graph illustrating the mean square error of lateral strain motion estimates, according to an embodiment of the disclosure.
Figure 31:
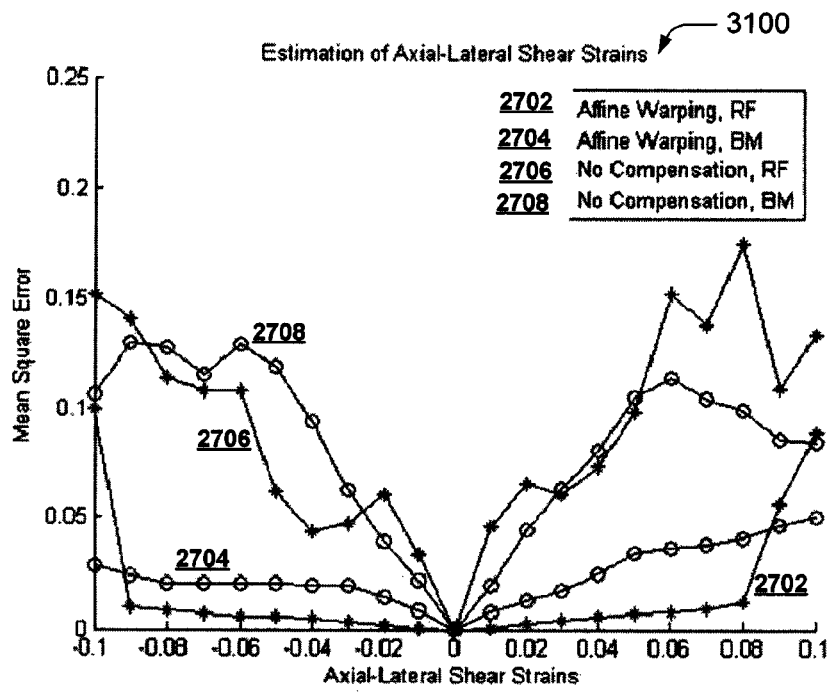
FIG. 31 is an example non-limiting graph illustrating the mean square error of axial-lateral shear strain motion estimates, according to an embodiment of the disclosure.
Figure 32:
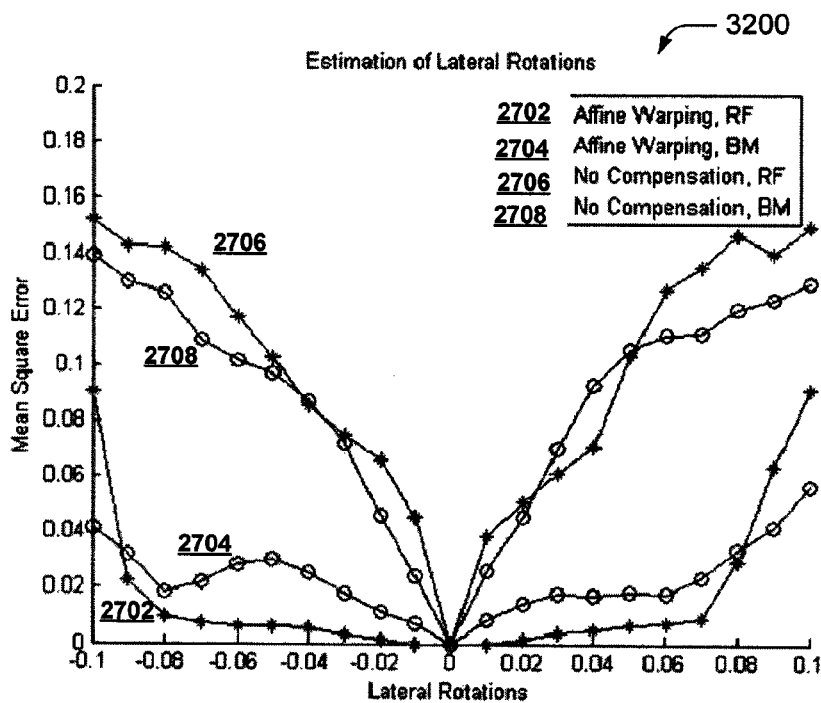
FIG. 32 is an example non-limiting graph illustrating the mean square error of lateral rotation motion estimates, according to an embodiment of the disclosure.

Referring now to FIGS. 30-32, illustrated are example mean square errors of motion estimation with respect to 3-D tissue motion in the three cases mentioned above. FIG. 30 corresponds to lateral compression/expansion; FIG. 31 corresponds to shearing along the axial-lateral plane; and FIG. 32 corresponds to lateral rotation. Affine warping RF is shown at element 2702, affine warping B mode is shown at element 2704, no compensation RF is shown at element 2706, and no compensation B mode is shown at 2708.

In all three cases, mean square errors remain close to zero for the affine warping method using RF images, except some extreme cases (e.g., applied shear strain larger than 8% for the case of axial-lateral shearing and applied rotation angle larger than 0.07 rad for the case of lateral rotation). On the other hand, mean square errors may gradually increase for the affine warping method using B mode images (e.g., in the case of lateral compression/expansion), mainly because speckle patterns are not enough for robust strain estimation in B mode images. Tissue motion estimation may fail if feature motion decorrelation is not compensated, while the performance of the direct correlation method using B mode images is slightly better than the direct correlation method using RF images, because speckle pattern variations are much smaller in B mode images.

In a two-dimensional phantom data experiment, a comparative study on the affine warping method using B mode images and the affine warping method using RF images was conducted. The performance of B mode affine warping and RF images affine warping were compared under the compression of the tissue mimicking gelatin phantom. The phantom is compressed down by 2 percent and 5 percent, respectively. In the 2 percent case, tissue deformation is not large and robust estimation of tissue motion is not extremely difficult, while in the 5 percent case, tissue deformation is large and considered to be difficult.

Figure 33:
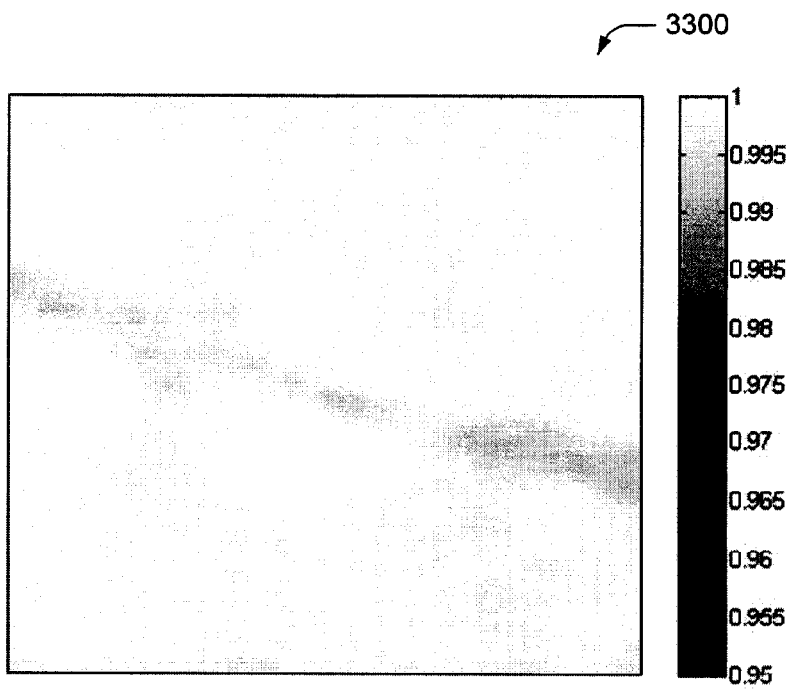
FIG. 33 is an example non-limiting correlation coefficient estimation for the affine warping method under 2% compression of a two dimensional tissue mimicking phantom.

Referring now to FIG. 33, illustrated is an example non-limiting correlation coefficient for the affine warping method for B mode under 2% compression of a two dimensional tissue mimicking phantom. Compared to FIG. 16, which shows the correlation coefficient for the affine warping method for RF mode under 2% compression of a two dimensional tissue mimicking phantom, the affine warping method of FIG. 33, which uses B mode images, is able to achieve mean correlation coefficients close to 1 everywhere (e.g., around 0.995 even if it is in the channel region), while correlation coefficients drop dramatically in the channel region for the affine warping method using RF images (note that for the affine warping method using B mode images, slightly lower correlation coefficients in the channel region is also observed). This is partially because speckle pattern variations are much smaller in B mode images than in RF images.

Figure 34:
FIG. 34 is an example non-limiting axial strain estimation for the affine warping method under 2% compression of a two dimensional tissue mimicking phantom.

Referring now to FIG. 34, illustrated is an example non-limiting axial strain estimation for the affine warping method for B mode under 2% compression of a two dimensional tissue mimicking phantom. FIG. 16 which illustrates an axial strain estimation for the affine warping method for RF under 2% compression of a two dimensional tissue mimicking phantom. FIGS. 34 and 16 provide a qualitative validation of axial strain estimation for the affine warping method for B mode and RF images.

Axial strains are deduced directly from the optimal motion parameters for the affine warping method using RF images, while for the affine warping method using B mode images, speckle patterns are not enough for robust strain estimation and the axial strains are produced indirectly from the estimated displacements. The affine warping methods using both B mode images and RF images are able to characterize the hard inclusion and the channel region correctly, demonstrating a similar performance of strain estimation between the affine warping method using B mode images and RF images. Although speckle patterns are not rich enough (i.e., without enough fine textures) for robust strain estimation in B mode images, tissue displacements can be estimated robustly. Axial strain estimations derived from differentiation of estimated tissue displacements show reasonably good performance. Axial strain estimations in the gelatin region as gradients of estimated displacements are not smooth enough. This is partially because the gradient operation amplifies noises in the estimation.

Figure 35:
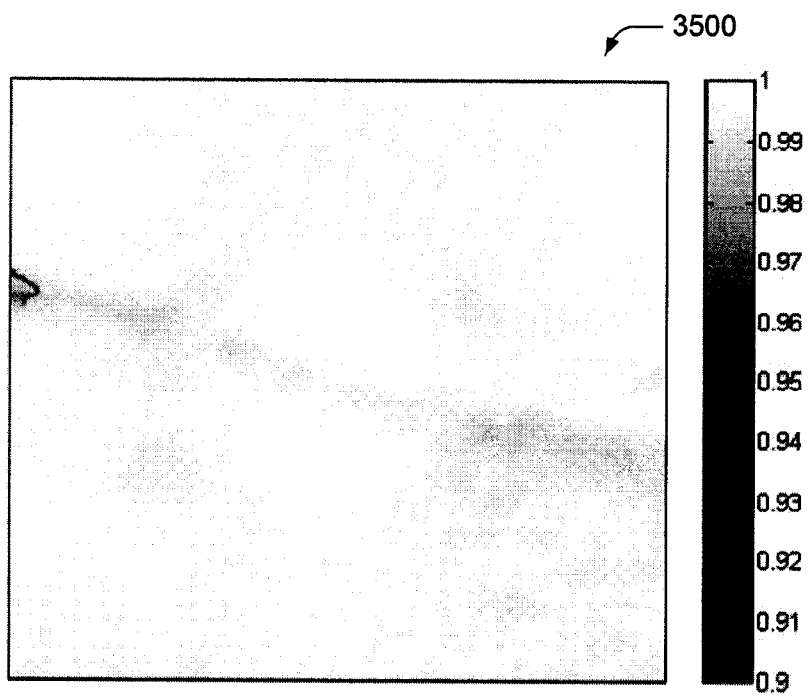
FIG. 35 is an example non-limiting correlation coefficient for the affine warping method under 5% compression of a two dimensional tissue mimicking phantom.

Referring now to FIG. 35, illustrated is an example non-limiting correlation coefficient for the affine warping method for B mode under 5% compression of a two dimensional tissue mimicking phantom. Compared to FIG. 22, which shows the correlation coefficient for the affine warping method for RF mode under 5% compression of a two dimensional tissue mimicking phantom, the affine warping method using B mode images of FIG. 35 is able to achieve mean correlation coefficients close to 1 everywhere (e.g., around 0.99even if it is in the channel region), while correlation coefficients drop dramatically in the channel region for the affine warping method using RF images (note that for the affine warping method using B mode images, correlation coefficients are also slightly smaller in the channel region).

Figure 36:
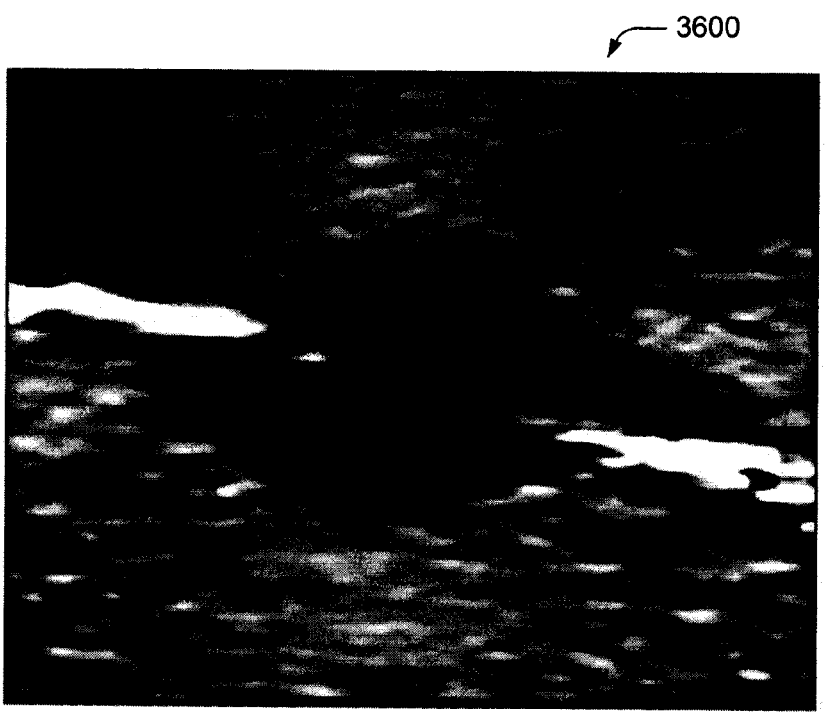
FIG. 36 is an example non-limiting axial strain estimation for the affine warping method under 5% compression of a two dimensional tissue mimicking phantom.

Referring now to FIG. 36, illustrated is an example non-limiting axial strain estimation for the affine warping method for B mode under 5% compression of a two dimensional tissue mimicking phantom. FIG. 25 which illustrates an axial strain estimation for the affine warping method for RF under 5% compression of a two dimensional tissue mimicking phantom. FIGS. 36 and 25 provide a qualitative validation of axial strain estimation for the affine warping method for B mode and RF images.

Axial strains are determined directly from the optimal motion parameters for the affine warping method using RF images, while for the affine warping method using B mode images, the axial strains are produced from the estimated displacements. The affine warping methods using both B mode images and RF images are able to characterize the hard inclusion and the channel region correctly, demonstrating that a similar performance of strain estimation between the affine warping method using B mode images and RF images, even when tissue motion is very large. In such difficult case, tissue displacements is estimated robustly, and axial strain estimations derived from differentiation of estimated tissue displacements show reasonably good performance. Axial strain estimations in the gelatin region as gradients of estimated displacements are not smooth enough. This is partially because the gradient operation amplifies noises in the estimation.

Object Tracking

In accordance with one or more embodiments described in this disclosure, various non-limiting aspects are described in connection with object tracking through segmentation without user interaction or training data. An object can be tracked through an image sequence by converting the image sequence into an input matrix, approximating the input matrix with a low rank matrix having a lower rank than the input matrix, and detecting outliers of the input matrix. The outliers correspond to the tracked object.

Figure 37:
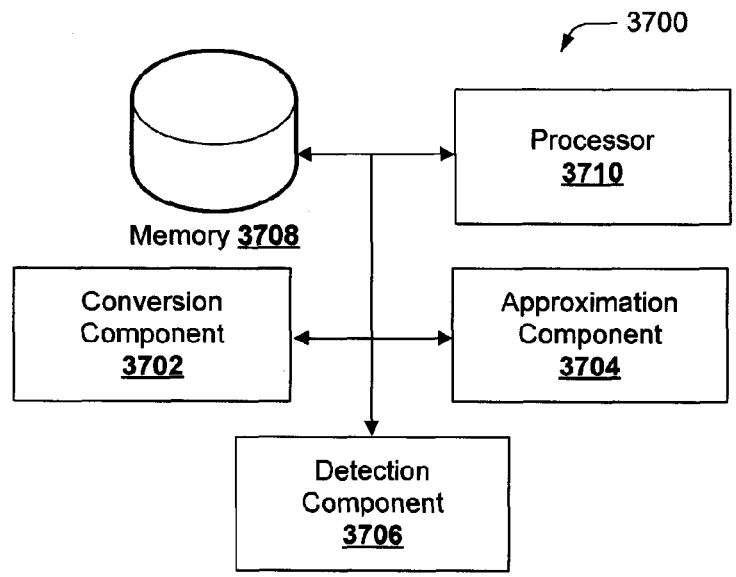
FIG. 37 illustrates an example non-limiting system that facilitates segmentation and tracking of a feature of an object within a sequence of images, according to an embodiment of the disclosure.

Referring now to the drawings, with reference initially to FIG. 37, illustrated is an example non-limiting system 3700 that facilitates segmentation and tracking of a feature of an object within a sequence of images, according to an embodiment of the disclosure. The sequence of images can include two dimensional images or three dimensional volumes. The sequence of images can also be an image/subimage sequence. The image sequence can be an ultrasound image sequence, a computed tomography image sequence, a magnetic resonance imaging sequence, or any other type of imaging sequence. In an embodiment, the image sequence corresponds to an echocardiographic image sequence and the feature of the object to be tracked is the mitral leaflet.

The sequence of images is processed by converting the sequence into an input matrix. The system 3700 includes a conversion component 3702 that facilitates conversion of the sequence of images to the input matrix. The column index of the input matrix corresponds to the frame index of the sequence of images. A column of the input matrix is a vectorized image related to the sequence of images. In an embodiment, each column of the input matrix is a vectorized image related to the sequence of images.

The input matrix is approximated by a low rank matrix through a low rank approximation. The system 3700 also includes an approximation component 3704 that performs the low rank approximation. The approximation component 3704 approximates the input matrix with a low rank matrix that has a lower rank than the input matrix.

The input matrix can be approximated by a low rank matrix and a set of outliers. The low rank matrix corresponds to background portions of the image sequence. Background portions of the image correspond to parts of the image other than the feature of the object to be tracked. Outliers of the low rank matrix correspond to the feature of the object to be tracked. The system 3700 also includes a detection component 3706 that detects one or more outliers of the low rank matrix that correspond to the feature of the object to be tracked.

The system 3700 also includes a memory 3708 that stores the components 3702-3706 and a processor 3708 that facilitates execution of one or more of the components 3702-3706.

Figure 38:
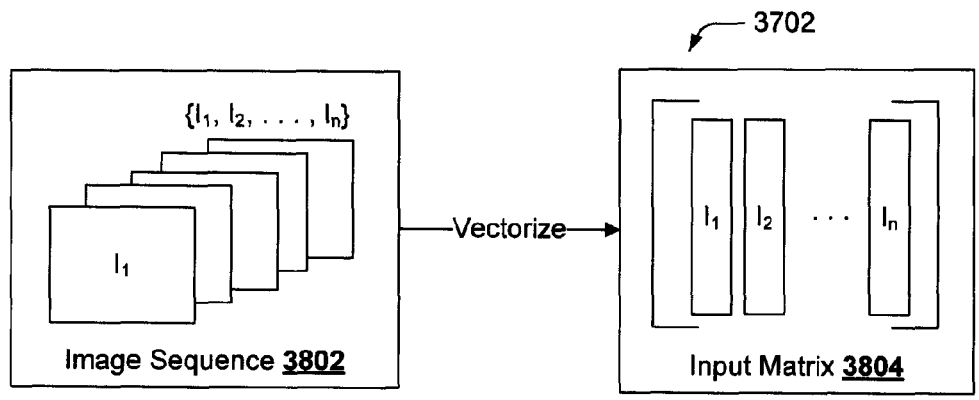
FIG. 38 illustrates an example non-limiting system that facilitates converting an image sequence into an input matrix, according to an embodiment of the disclosure.

Referring now to FIG. 38, illustrated is an example non-limiting system (corresponding to conversion component 3702) that facilitates converting an image sequence 3802 into an input matrix 3804, according to an embodiment of the disclosure. The conversion component 3702 facilitates conversion of an image sequence 3802 to an input matrix 3804.

The image sequence 3802 has a frame index $\{I_1, I_2, \ldots I_n\}$. The image sequence 3802 is converted to the input matrix 3804 with the column index if the input matrix 3804 corresponding to the frame index $\{I_1, I_2, \ldots I_n\}$ of the image sequence. Each column of the input matrix 3804 is a vectorized image from image sequence 3802. The images from the image sequence 3802 are vectorized by stacking intensity values of image pixels into a column vector in a pre-defined order. In an embodiment, the pre-defined order is a column-wise scanning order.

Figure 39:
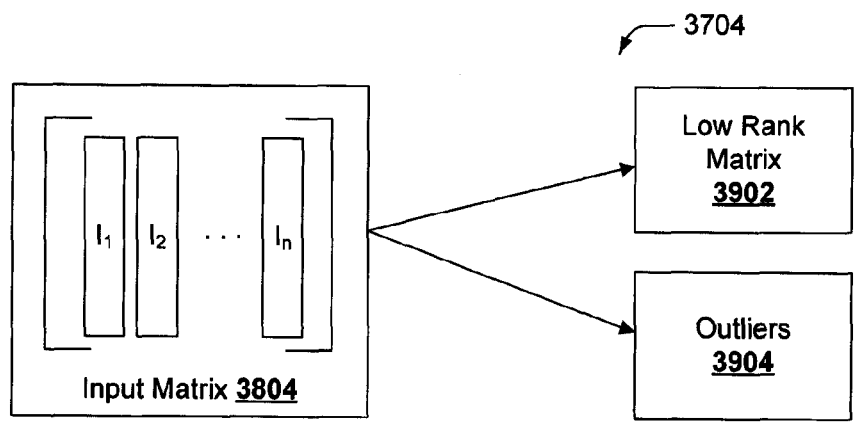
FIG. 39 illustrates an example non-limiting system that facilitates modeling an input matrix as a low rank matrix and a set of outliers, according to an embodiment of the disclosure.

Referring now to FIG. 39, illustrated is an example non-limiting system (corresponding to approximation component 3704) that facilitates modeling an input matrix 3804 as a low rank matrix 3902 and a set of outliers 3904, according to an embodiment of the disclosure. The approximation component 3704 performs a low rank approximation, approximating the input matrix 3804 with a low rank matrix 3902 that has a lower rank than the input matrix and a set of outliers 3904.

More bases are used to represent the feature of the object than the rest of the object. Because more bases are used to represent the feature of the object, the outliers 3904 of the low rank matrix 3902 can be assumed to correspond to the location of the feature of the object.

Figure 40:
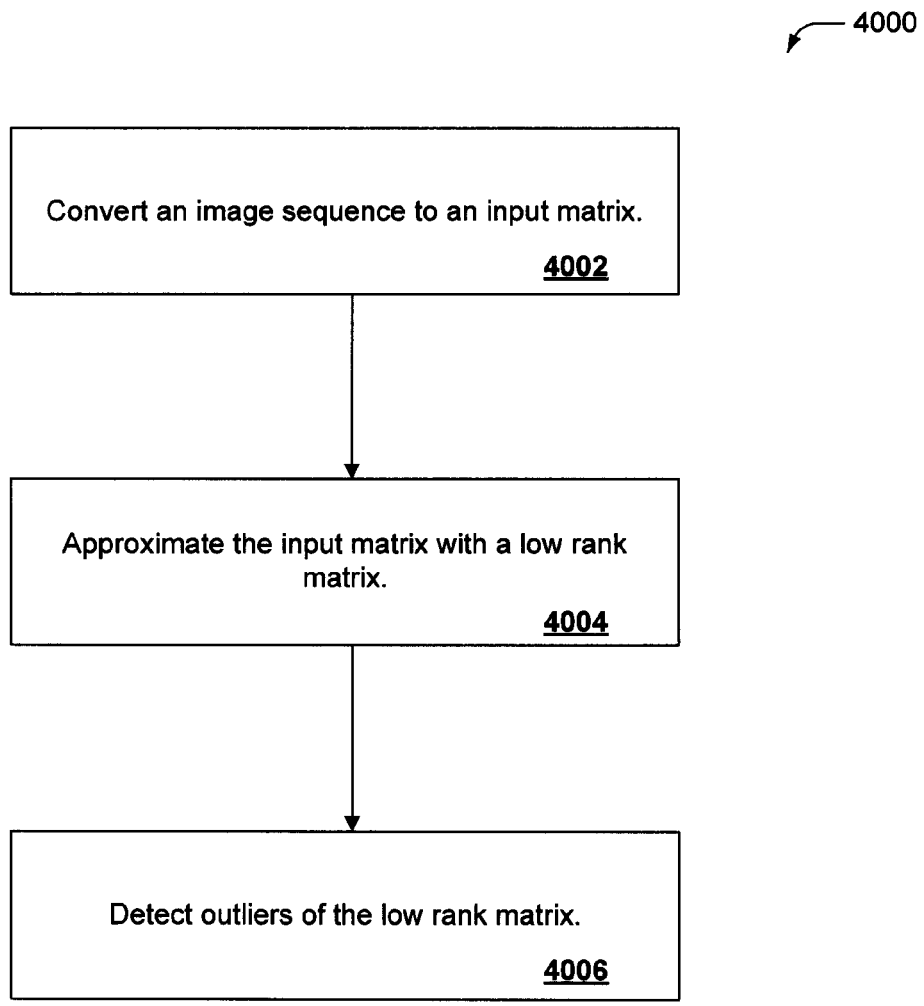
FIG. 40 is an example non-limiting process flow diagram of a method that facilitates analysis of a series of images, according to an embodiment of the disclosure.
Figure 41:
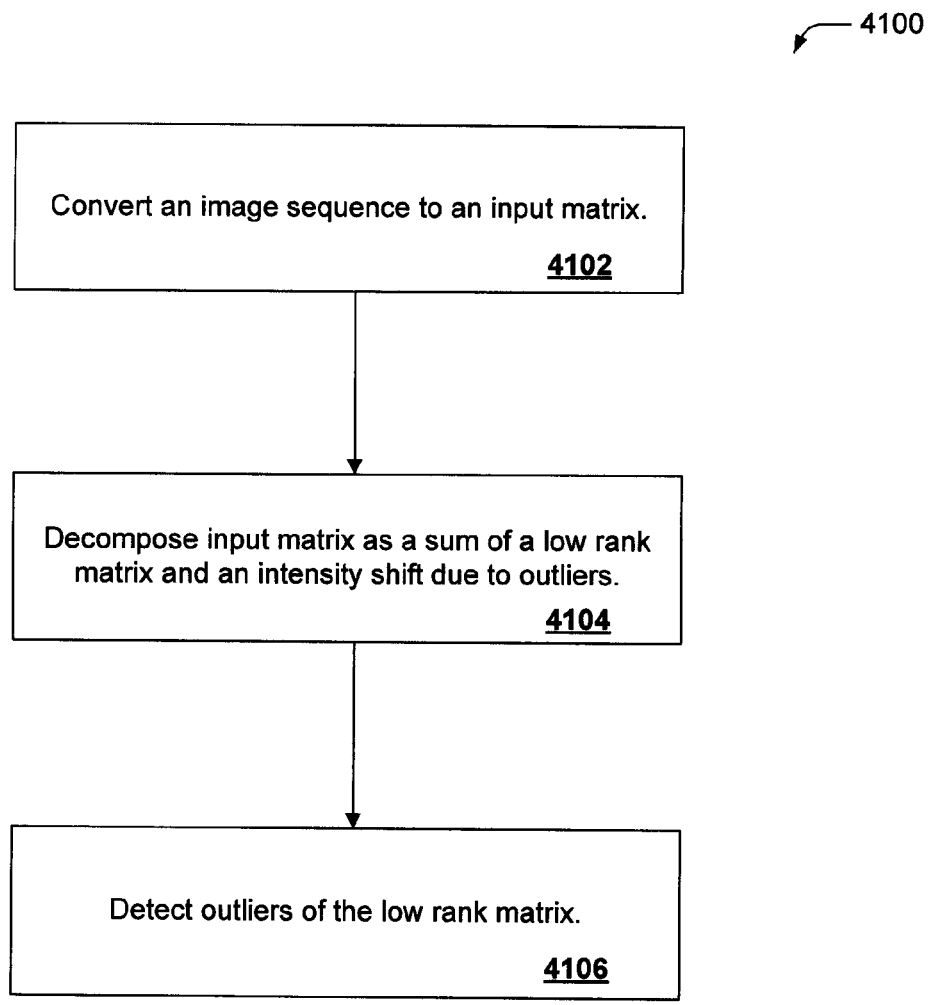
FIG. 41 is an example non-limiting process flow diagram of a method that facilitates detection of outliers corresponding to a feature of an image, according to an embodiment of the disclosure.
Figure 42:
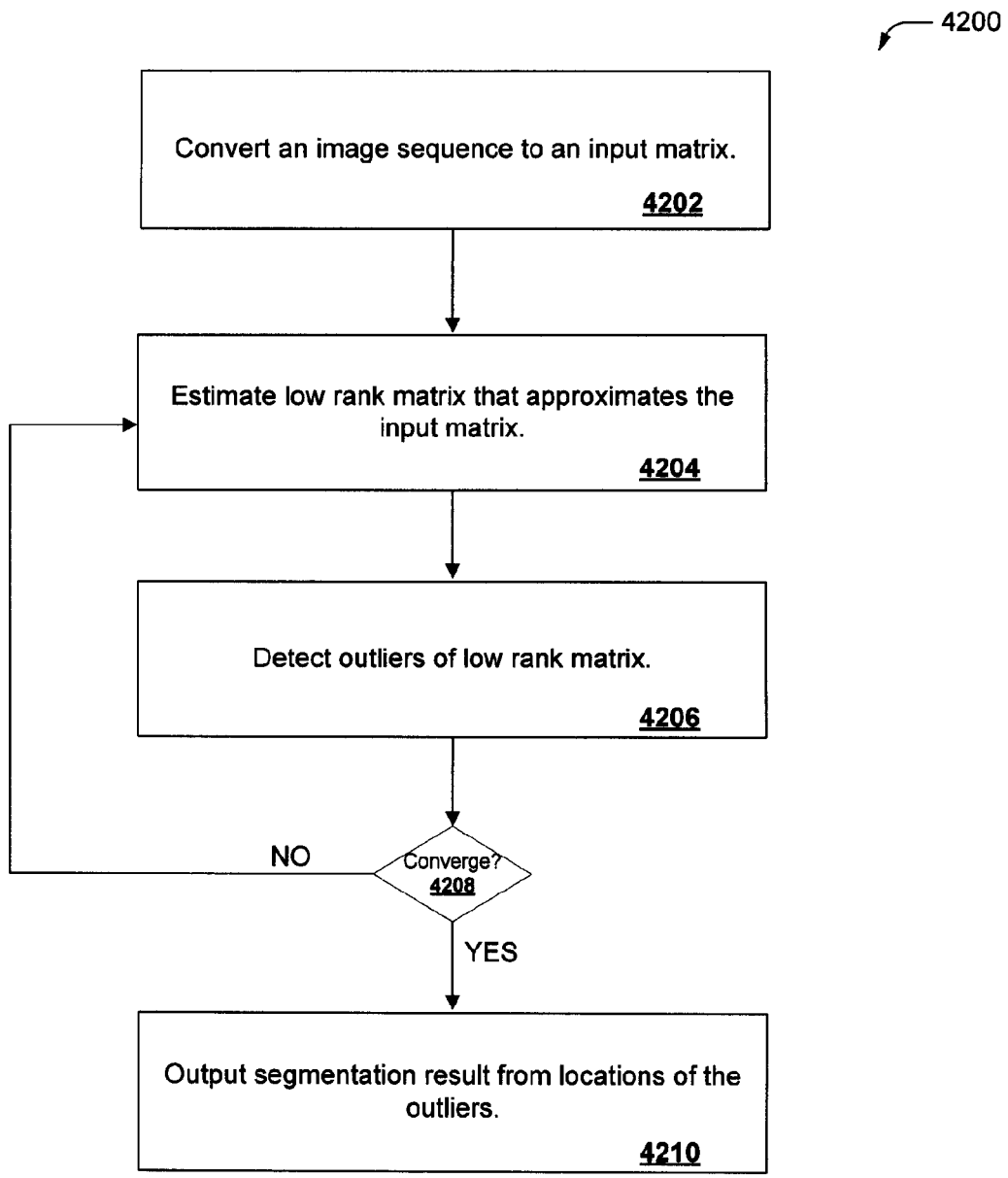
FIG. 42 is an example non-limiting process flow diagram of a method that facilitates segmentation and tracking of a feature of an image through iteratively minimizing an energy function, according to an embodiment of the disclosure.

FIGS. 40-42 illustrate methods and/or flow diagrams in accordance with embodiments of this disclosure. For simplicity of explanation, the methods are depicted and described as a series of acts that can be executed by a system including a processor. However, acts in accordance with this disclosure can occur in various orders and/or concurrently, and with other acts not presented and described in this disclosure. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be further appreciated that the methods disclosed in this specification are capable of being stored on an article of manufacture to facilitate transporting and transferring such methods to hardware devices.

Referring now to FIG. 40, illustrated is an example non-limiting process flow diagram of a method 4000 that facilitates analysis of a series of images, according to an embodiment of the disclosure. The series of images can include two dimensional images or three dimensional volumes. The series of images can also be an image/subimage sequence. The series of images can be an ultrasound image sequence, a computed tomography image sequence, a magnetic resonance imaging sequence, or any other type of imaging sequence. In an embodiment, the series of images corresponds to an echocardiographic image sequence and the method 4000 facilitates tracking of the mitral leaflet.

At 4002, an image sequence is converted to an input matrix by a system including a processor. A column of the input matrix is a vectorized image related to the image sequence. At 4004, the input matrix can be approximated, by the system, with a low rank matrix. At 4006, one or more outliers of the input matrix can be detected by the system. The one or more outliers correspond to an object to be tracked in the series of images.

Referring now to FIG. 41, illustrated is an example non-limiting process flow diagram of a method 4100 that facilitates detection of outliers corresponding to a feature of an image, according to an embodiment of the disclosure. At 4102, an image sequence is converted, by a processor, to an input matrix. At element 4104, the input matrix can be decomposed as a sum of a low rank matrix and an intensity shift due to outliers. At element 4106, the outliers of the low rank matrix can be detected based on the intensity shift due to outliers.

According to an embodiment, method 4100 is employed to track and segment the mitral leaflet from an ultrasound (echocardiographic) image sequence. Tracking the mitral leaflet from an ultrasound sequence is difficult due to lack of reliable features, as well as fast and irregular motion of the mitral valve. In ultrasound images, the mitral leaflet shares similar intensity and texture values with other tissues, such as myocardium. Additionally, the feature quality, such as edges, shows a large variation due to factors including probe orientation, acoustic speckle, signal dropout, acoustic shadows, and the like.

Object tracking usually relies on the computation of optical flow to find feature-point correspondence between frames. However, motion analysis in ultrasound sequences is difficult and unreliable due to the feature-motion decorrelation problem. Motion analysis is more challenging under conditions of fast motion, large deformation, and low frame rate, which is the case when imaging the mitral valve, especially in the case of three dimensional imaging of the mitral valve.

Method 4100 provides an automatic mitral leaflet tracking method without additional user interaction or training data. At 4102, an echocardiographic image sequence is converted, by a processor, to an input matrix. Frames of the echocardiographic image sequence are vectorized, and the vectorized images correspond to columns of the input matrix. At element 4104, the input matrix is decomposed as a sum of a low rank matrix and an intensity shift due to outliers. The low rank matrix corresponds to background —like the myocardium. More bases are used to describe the mitral leaflet motion compared with the myocardium motion, so the outliers of the input matrix correspond to pixels of the mitral leaflet. At element 4106, the outliers of input matrix can be detected based on the intensity shift due to outliers and the location of the mitral leaflet can be segmented from the myocardium and tracked through the image sequence.

The echocardiographic sequence can be composed of n images. At 4102, the echocardiographic sequence of n images is converted to the input matrix represented by $D \in R^{m \times n}$, where m is the number of pixels in the image and n is the number of images.

If no motion exists in the sequence, all images of the echocardiographic sequence are identical. Accordingly, when no motion exists, ignoring the noise in the images, rank(D)=1.

If motion does exist in the sequence, as is more realistic since cardiac motion exists, the image and the images change within a cardiac cycle, rank(D)>1. However, due to the correlation among the frames, the energy distribution in the matrix spectrum (the set of eigenvalues of the matrix) of D will concentrate on a limited number of principle components.

The cumulative distribution function (cdf) of the spectral energy of D is defined as follows:

$$cdf(k) = \frac{\sum_{j=1}^{k} \sigma_j^2}{\sum_{j=1}^{r} \sigma_j^2},$$

where r=min(m,n) and $\sigma_1, \ldots, \sigma_r$ are singular values of D in descending order. The cdf exceeds 95% for an echocardiography sequence when k>2.

The cdfs corresponding to different regions are different. For example, the valve region including the mitral leaflet has different corresponding cdfs than the cdfs corresponding to the myocardium or the blood pool. The cdf for the valve region including the mitral leaflet is lower than that of the myocardium or the blood pool. Accordingly, spectral distribution of the valve region is more spread out. This is attributed to the fact that the mitral leaflet moves much faster with larger tissue deformation compared with myocardium that moves smoothly across a cardiac cycle.

Thus, more principle components are used to describe the image variation caused by the complex motion of the mitral leaflet. In other words, given a fixed K, the residue of fitting the valve region with a rank-K matrix will be much larger compared to the residue of fitting other regions. Accordingly, at element 4104, the input matrix is decomposed as a sum of a low rank matrix and an intensity shift due to outliers. The low rank matrix corresponds to background —like the myocardium or the blood pool. Since more principle components are used to describe the image variation caused by the complex motion of the mitral leaflet, more bases are used to describe the mitral leaflet motion compared with the myocardium motion, so the outliers of the input matrix correspond to pixels of the mitral leaflet.

In other words, at element 4104, the input matrix is decomposed as a sum of the low rank matrix, an intensity shift due to the outliers, and random noise:

$D=B+E+\epsilon,$ where D is the input matrix, B is the low rank matrix, E is the intensity shift caused by the one or more outliers and $\epsilon$ is the random noise.

In an embodiment, the random noise can be neglected, so the input matrix can be decomposed as the sum of the low rank matrix and an intensity shift due to the outliers:

$D=B+E.$

At element 4106, the outliers (with intensity shift E) of the input matrix (B) can be detected based on the intensity shift due to outliers and the location of the mitral leaflet can be segmented from the myocardium and tracked through the image sequence.

The outliers can be detected at element 4106 by comparing an intensity of an entry of the input matrix to a corresponding intensity of the low rank matrix. An outlier is determined when the intensity of the entry of the input matrix differs from the corresponding intensity of the low rank matrix.

Segmentation and tracking of a feature of an image are facilitated through minimizing and/or optimizing an energy function, according to an embodiment of the disclosure. The energy function, according to an embodiment, has four terms:
Term 1: Describing the difference between the input matrix and the low rank matrix (e.g., the sum of squared residue of fitting the input with the low rank matrix);
Term 2: Measuring a property of the low rank matrix (e.g., the rank of the low rank matrix);
Term 3: Measuring a property of absolute values of the outliers (e.g., the number of outliers); and
Term 4: Assuming that neighboring pixels belong to a same class (e.g., outliers/non-outliers).

It will be understood that the energy function can have alternate or more terms. Additionally, the energy function can omit one or more of the terms. For example, according to an embodiment, the energy function includes Term 1, Term 2, and Term 3 without including Term 4.

Minimizing or optimizing the energy function facilitates approximating the input matrix as a low rank matrix and detecting outliers of the input matrix. The minimizing or optimizing can be done, by the system, iteratively until a convergence is reached between the approximating and the detecting. An iterative method is shown in FIG. 42.

Referring now to FIG. 42, illustrated is an example non-limiting process flow diagram of a method 4200 that facilitates segmentation and tracking of a feature of an image through iteratively minimizing an energy function, according to an embodiment of the disclosure. At element 4202, an image sequence is converted to an input matrix. An energy function is minimized or optimized through an iterative process from elements 4204-4208. In the iterative process, at element 4204, a low rank matrix is estimated to approximate the input matrix. According to an embodiment, this estimation can occur by matrix completion. At element 4206, outliers of the low rank matrix can be detected. In an embodiment, this detection can occur by graph cuts. At element 4208, the estimation and detection can be iterated until a convergence is reached. At element 4210, a segmentation result can be output from the locations of the outliers after convergence is reached.

Figure 43:
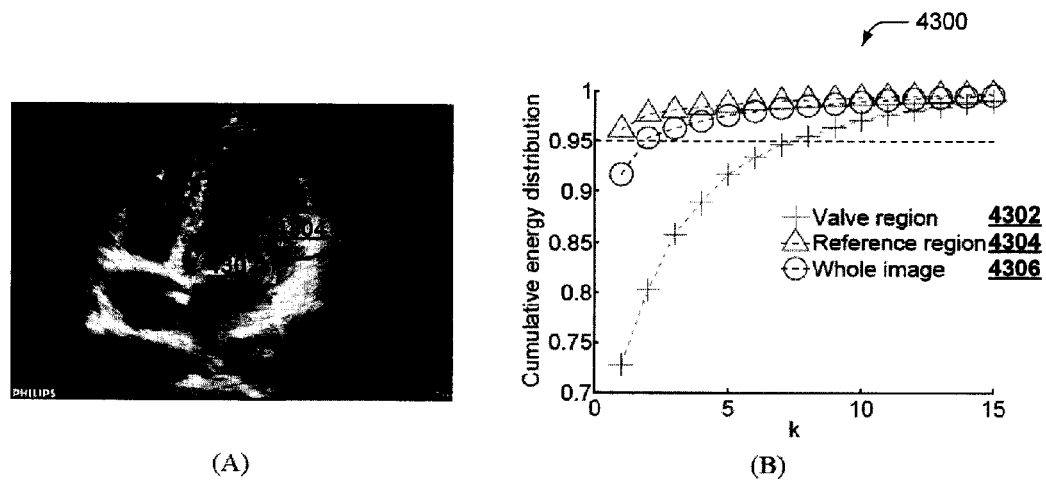
FIG. 43 is an example non-limiting illustration showing the feasibility of the matrix spectral analysis procedure, according to an embodiment of the disclosure.
Figure 45:
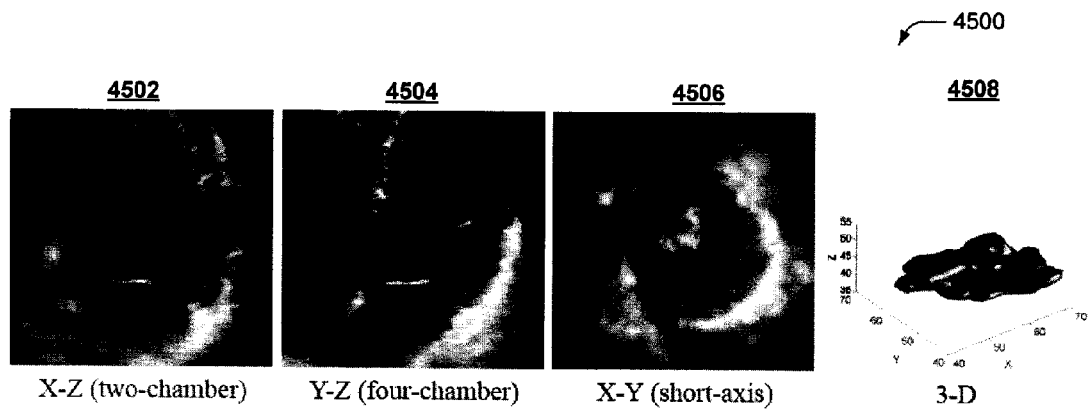
FIG. 45 is an example non-limiting results of tracking the mitral valve via matrix spectral analysis of a sequence of three dimensional echocardiographic images, according to an embodiment of the disclosure.
Figure 44:
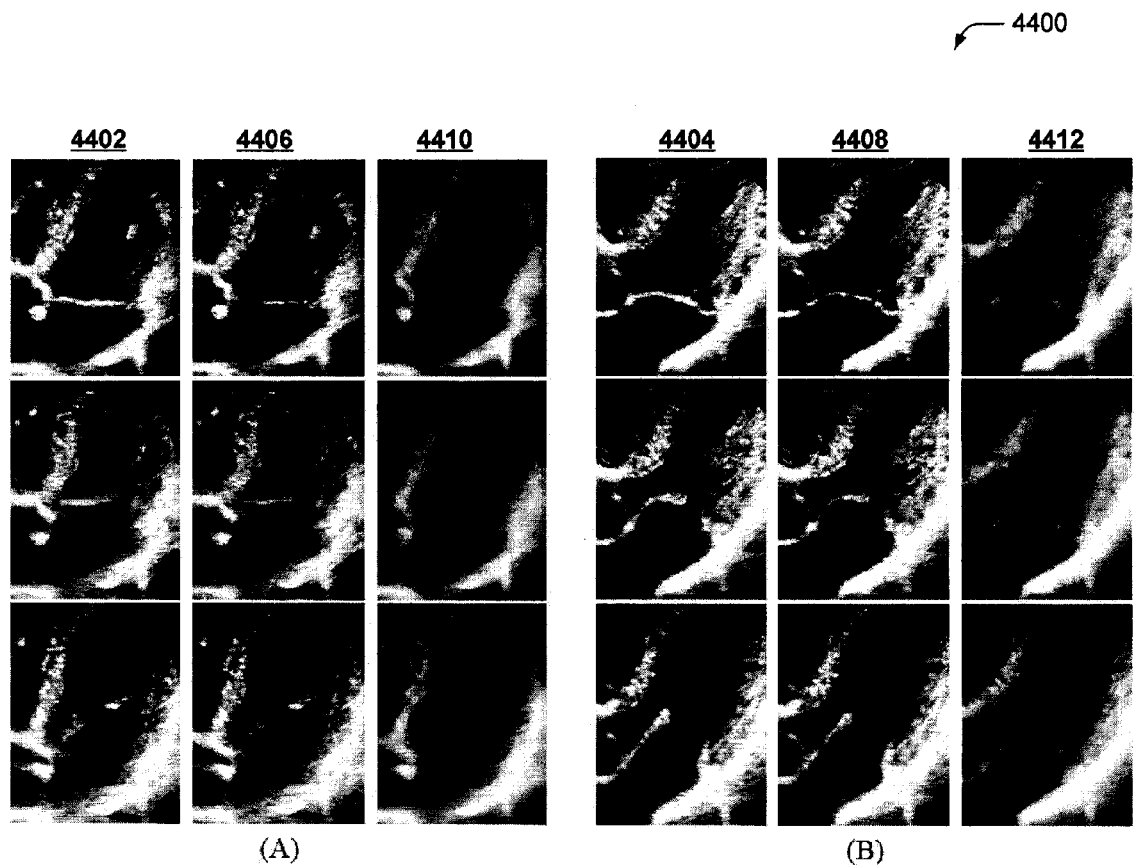
FIG. 44 is an example non-limiting results of tracking the mitral valve via matrix spectral analysis of a sequence of two dimensional echocardiographic images, according to an embodiment of the disclosure.

FIGS. 43-45 illustrate examples of mitral leaflet tracking from an echocardiographic sequence according to the systems and methods described above. FIG. 43 shows the feasibility of the matrix spectral analysis procedure for mitral leaflet tracking. FIGS. 44 and 45 show example results of mitral leaflet tracking using transthoracic echocardiographic (TTE) data.

FIG. 43 is an example non-limiting illustration 4300 showing the feasibility of the matrix spectral analysis procedure, according to an embodiment of the disclosure. Manually segmented regions of the valve 4302, the myocardium and blood pool (reference region) 4304, and the whole image 4306 is shown in (A). A plot of the cumulative distribution function of spectral energy versus k for the three regions 4302-4306 is shown in (B).

As shown in (B), the cdfs corresponding to the different regions 4302-4306 are different. The cdfs of the reference region 4304 and the whole image 4306 are higher than the cdfs of the valve region 4302. Due to the cdfs of the valve region 4302 being lower than the cdfs of the myocardium and blood pool, the spectral distribution of the valve region is more spread out than the spectral distribution of the myocardium and blood pool.

The spectral distribution of the valve region is more spread out than the spectral distribution of the myocardium and blood because the mitral leaflet moves much faster with larger tissue deformation compared to myocardium that moves smoothly across a cardiac cycle. Thus, more principle components are used to describe the image variation caused by the complex motion of the mitral leaflet. This shows that representing the image as a low rank matrix and an intensity shift due to outliers is appropriate for isolating the mitral leaflet. The low rank matrix corresponds to background—like the myocardium or the blood pool. Since more principle components are used to describe the image variation caused by the complex motion of the mitral leaflet, more bases are used to describe the mitral leaflet motion compared with the myocardium motion.

The echocardiographic sequence can be well approximated by a low-rank matrix except for the mitral leaflet, which occupies a relatively small and connected region in the images. Thus, the problem of mitral leaflet segmentation can be formulated as outlier detection in the low-rank representation.

The following notations are used for description. Let ij denote the i-th pixel in the j-th frame of the sequence and S be a binary matrix denoting the outlier support, i.e. $S_{ij}=1$ if ij is the mitral leaflet pixel and $S_{ij}=0$ otherwise. $P_s(X)$ represents the orthogonal projection of a matrix X onto the linear space of matrices supported by S:

$$\mathcal{P}_S(X)(i,j) = \begin{cases} 0, & \text{if } S_{ij} = 0 \\ X_{ij}, & \text{if } S_{ij} = 1, \end{cases}$$

and $P_{S^\perp}(X)$ be its complementary projection, i.e. $P_S(X)+P_{S^\perp}(X)=X$.

Three norms of a matrix X are used in the description.

$$\|X\|_1 = \sum_{ij} |X_{ij}|$$

denotes the $l_1$-norm.

$$\|X\|_F = \sqrt{\sum_{ij} |X_{ij}^2|}$$

is the Frobenius norm. $\|X\|_*$ means the nuclear norm, i.e. sum of singular values.

The task is to give an optimal estimate to S that labels the outliers of the input matrix D with the low-rank model B. Since both B and S are unknown, it is required to estimate them simultaneously. The following energy can be minimized to estimate B and S:

$$\min_{B, S_{ij} \in \{0,1\}} \frac{1}{2} \|\mathcal{P}_S \perp (D-B)\|_F^2 + \beta \|S\|_1,$$

$$\text{s.t. } \text{rank}(B) \le K,$$

where K is a predefined constant. The first term penalizes the fitting residue for the non-valvular region, while the second term regularizes the sparsity of the mitral leaflet pixels.

Since the leaflet pixels should be contiguous in the image sequence both spatially and temporally, a smoothness regularizer is introduced on S. Consider a graph G=(V,E), where V is the set of vertices denoting all m×n pixels in the sequence and E is the set of edges connecting spatially and temporally neighboring pixels. Based on the first order Markov Random Fields (MRFs), the following energy is adopted to impose continuity on S:

$$\|Avec(S)\|_1 = \sum_{(ij,kl) \in \varepsilon} \omega_{ij,kl} |S_{ij} - S_{kl}|,$$

where A is the weighted node-edge incidence matrix of G, and the weight $\omega_{ij,kl}$ is defined as follows:

$$\omega_{ij,kl} = \begin{cases} e^{-\frac{|D_{ij}^G - D_{kl}^G|^2}{2\mu^2}}, & \text{if } ij \text{ and } kl \text{ are spatial neighbors,} \\ \omega_t, & \text{if } ij \text{ and } kl \text{ are temporal neighbors.} \end{cases}$$

Here, $D^G$ is the Gaussian smoothed image sequence, μ is the standard deviation of $D_{ij}^G - D_{kl}^G$ for spatial neighbors, and $\omega_t$ is the weight for temporal links. Introducing the spatially-varying $\omega_{ij,kl}$ makes use of the edge information to improve segmentation.

To make the energy minimization tractable, the rank operator is relaxed on B with the nuclear norm, which has proven to be an effective convex surrogate of the rank operator. Adding the smoothness regularizer and writing $$\min_{B, S_{ij} \in \{0,1\}} \frac{1}{2} \|\mathcal{P}_S \perp (D-B)\|_F^2 + \beta \|S\|_1,$$

$$\text{s.t. } \text{rank}(B) \le K,$$

in its Lagrangian form, the final form of the energy function is expressed as follows:

$$\min_{B,S} \frac{1}{2} \|\mathcal{P}_S \perp (D-B)\|_F^2 + \alpha \|B\|_* + \beta \|S\|_1 + \gamma \|Avec(S)\|_1.$$

The objective function defined in above is non-convex and it includes both continuous and discrete variables. Joint optimization over B and S is extremely difficult. Hence, an alternating algorithm is adopted that separates the energy minimization over B and S into two steps.

In the B-step, S is fixed to be its previous estimate $\hat{S}$ and the energy in the objective function is minimized over B:

$$\min_B \frac{1}{2} \|\mathcal{P}_S \perp (D-B)\|_F^2 + \alpha \|B\|_*.$$

It turns out to be the matrix completion problem, which can be solved in polynomial time using, for example, the SOFT-IMPUTE algorithm.

In the S-step, B is fixed to be its previous estimate $\hat{B}$ and the energy in the objective function is minimized over S:

$$\min_S \frac{1}{2} \left\| \mathcal{P}_S \perp (D - \hat{B}) \right\|_F^2 + \beta \|S\|_1 + \gamma \|Avec(S)\|_1$$

$$= \min_S \frac{1}{2} \sum_{ij} (D_{ij} - \hat{B}_{ij})^2 (1 - S_{ij}) + \beta \sum_{ij} S_{ij} + \gamma \|Avec(S)\|_1.$$

The above combinatorial optimization problem can be solved exactly in polynomial time using graph cuts.

FIGS. 44 and 45 show results of the matrix spectral analysis procedure. FIG. 44 is an example non-limiting results of tracking the mitral valve via matrix spectral analysis of a sequence of two dimensional echocardiographic images, according to an embodiment of the disclosure. FIG. 45 is an example non-limiting results of tracking the mitral valve via matrix spectral analysis of a sequence of three dimensional echocardiographic images, according to an embodiment of the disclosure.

All sequences were acquired during a cardiac cycle using a Philips iE33 Ultrasound System with an S5-1 probe for two dimensional imaging (FIG. 44) and an X3-1 probe for three dimensional imaging (FIG. 45). The systems and methods were implemented in MATLAB running on a PC with a 3.4 GHz Intel i7 CPU and 8 GB RAM, taking about 30 seconds to analyze a two dimensional sequence (FIG. 44) and about 24.4 minutes to analyze a three dimensional sequence (FIG. 45). The efficiency can be improved, for example, by implementation in C or other programming languages or execution through GPU computing or other computing systems that facilitate parallel processing.

FIG. 44 shows two example results from two (A), (B) two dimensional echocardiographic image sequences. Each sequence has about 30 frames recording a cardiac cycle, with an image size of 225×300 pixels. Three frames during valve opening 4402 and 4404 are displayed from both (A) and (B) for simplicity of illustration and description.

The mitral leaflet was detected (circled in each frame 4406 and 4408) as outliers of the input matrix. The low rank representation captured the global motion of myocardium, as shown in each frame 4410 and 4412.

The contour of the valve generated from the automatic method was quantitatively compared to the manual tracing of the valve. The mean absolute distance (MAD) was calculated between the contour of the valve generated from the automatic method and manual tracing. The MAD is 0.89±0.71 mm for the first sequence (A) and 0.94±0.18 mm for the second sequence (B). The MAD for (A) and (B) have the same order of magnitude with the resolution of the imaging system (~0.5 mm).

FIG. 45 shows an example result 4500 of mitral leaflet tracking from a three dimensional echocardiographic sequence. The three dimensional echocardiographic sequence includes 17 volumes, with 80×80×80 voxels per volume. The segmentation result on a selected volume is displayed.

Three orthogonal two dimensional slices across the mitral leaflet in the volumetric data 4502-4506 are shown with segmentation results superimposed on the two-dimensional slices. A three dimensional model 4508 of the mitral leaflet generated by surface rendering is also shown.

Computing Examples

Figure 46:
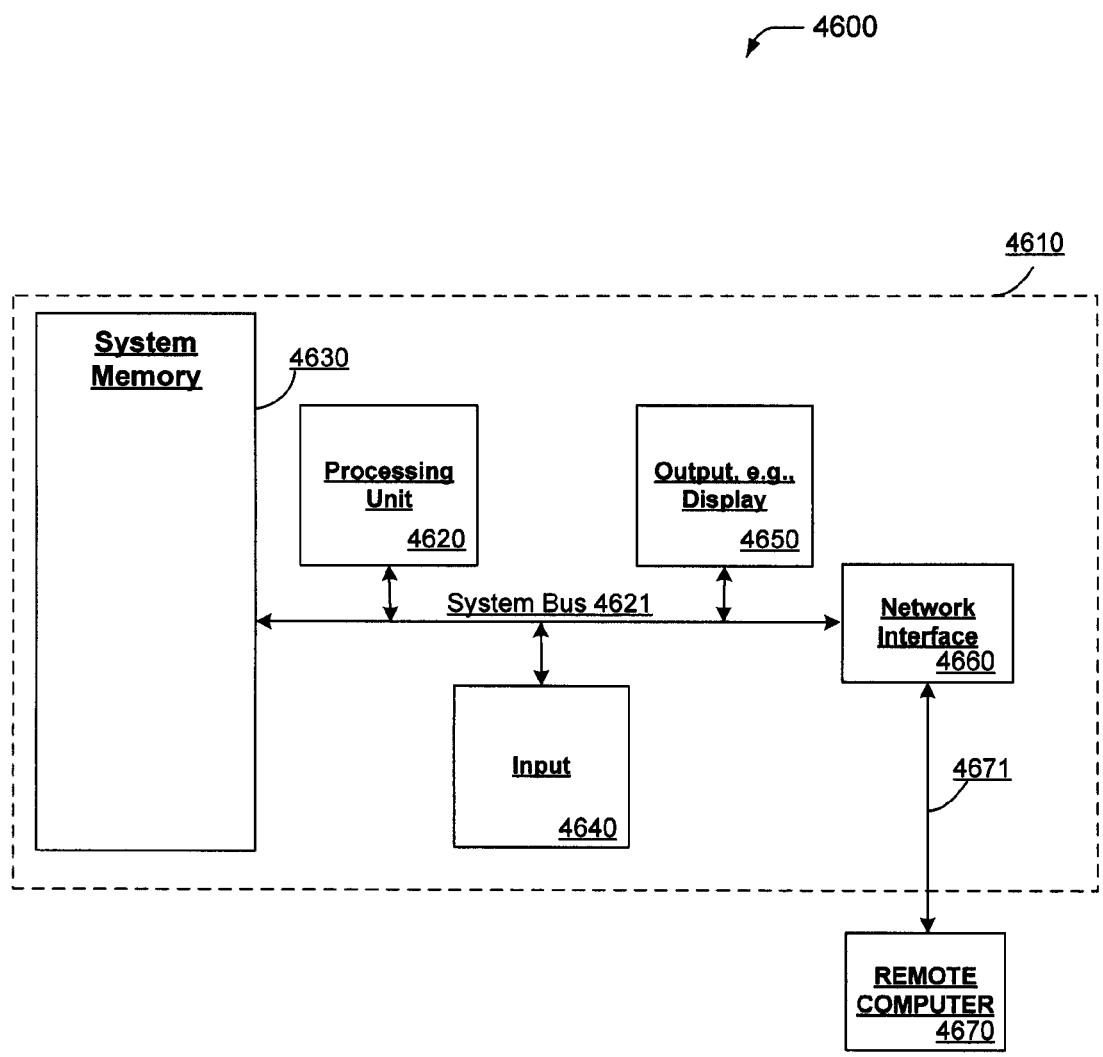
FIG. 46 illustrates an example computing environment in which the various embodiments described herein can be implemented.
Figure 47:
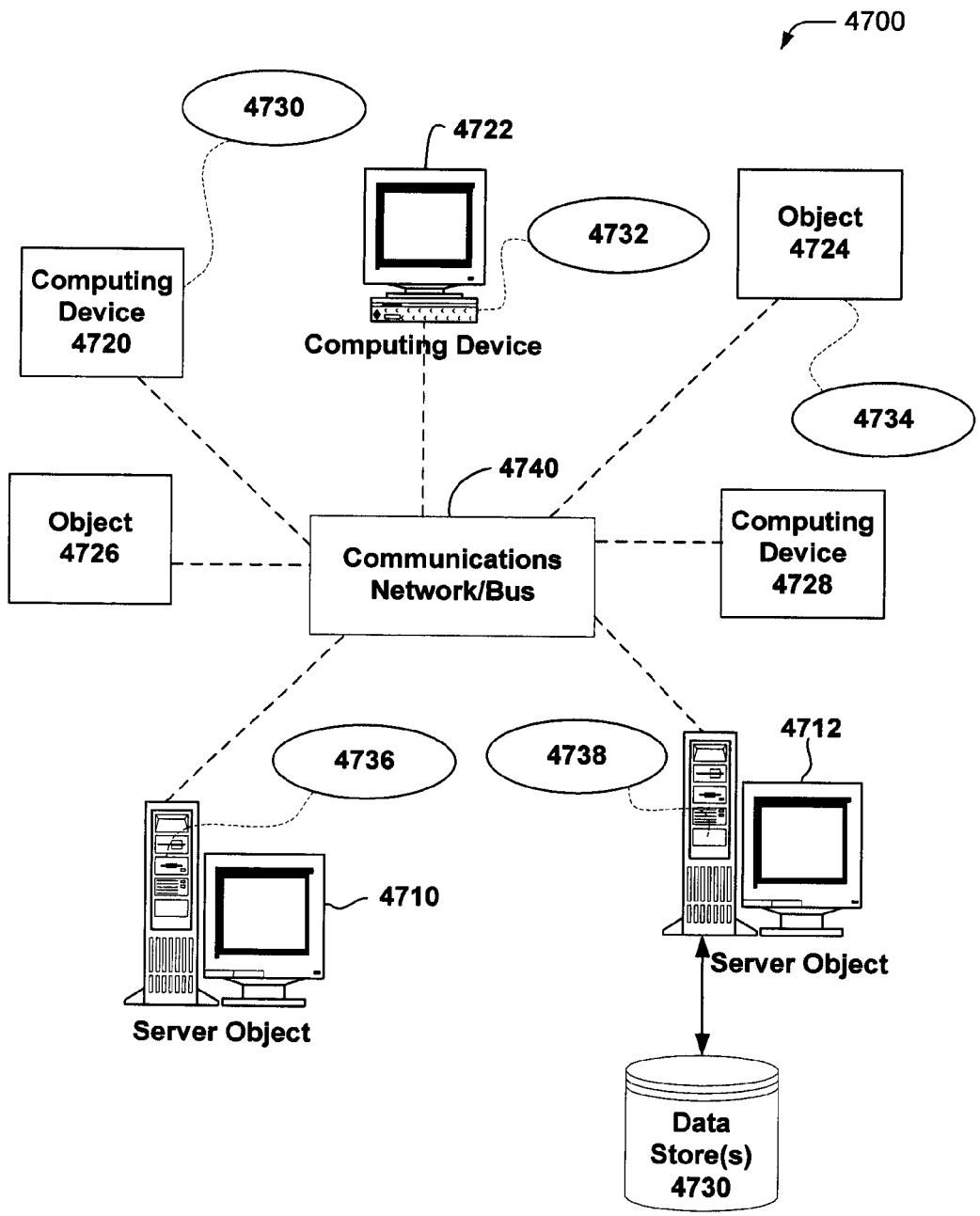
FIG. 47 illustrates an example of a computer network in which various embodiments described herein can be implemented.

The systems and methods that facilitate image analysis described above can be implemented in software, hardware, or a combination thereof. FIGS. 46 and 47 provide hardware context for the systems and methods described above. FIG. 46 illustrates a computing environment 4600 that can be utilized in connection with the systems and methods described above. FIG. 47 illustrates a computing network 4700 that can be utilized in connection with facilitating the systems and methods described above. It should be appreciated that artificial intelligence can also be utilized to implement the systems and methods described herein.

Referring now to FIG. 46, illustrated is an example of a suitable computing system environment 4600 in which one or more of the embodiments can be implemented. The computing system environment 4600 is just one example of a suitable computing environment and is not intended to suggest any limitation as to the scope of use or functionality of any of the embodiments. Neither should the computing environment 4600 be interpreted as having any dependency or requirement relating to any one or combination of components illustrated in the exemplary operating environment 4600.

With reference to FIG. 46, the computing system environment 4600 can include computer 4610, which can be a handheld or non-handheld computer. The computer 4610 can merely be capable of interfacing with an imaging device (e.g., a device that records or transfers images). However, the computing system environment 4600 can be any other computing device with a processor to execute the methods described herein and a display, such as a desktop computer, a laptop computer, a mobile phone, a mobile internet device, a tablet, or the like. Components of the computer 4610 can include, but are not limited to, a processing unit 4620, a system memory 4630, and a system bus 4621 that couples various system components including the system memory to the processing unit 4620. For example, the methods described herein can be stored in the system memory 4630 and executed by the processing unit 4620.

The computer 4610 can also include a variety of computer readable media, and can be any available media that can be accessed by computer 4610. The system memory 4630 can include computer storage media in the form of volatile and/or nonvolatile memory such as read only memory (ROM) and/or random access memory (RAM). By way of example, and not limitation, memory 4630 can also include an operating system, application programs, other program modules, and program data.

Computing devices typically include a variety of media, which can include computer-readable storage media and/or communications media, which two terms are used herein differently from one another as follows.

Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

A user can enter commands and information into the computer 4610 through input devices 4640, such as selecting a feature of an image. A monitor or other type of display device, e.g., touch screen or virtual display, can also connect to the system bus 4621 via an interface, such as output interface 4650.

The computer 4610 can operate in a networked or distributed environment using logical connections to one or more other remote computers, such as remote computer 4670. The remote computer 4670 can be a personal computer, a server, a router, a network PC, a peer device or other common network node, or any other remote media consumption or transmission device, and can include any or all of the elements described above relative to the computer 4610. The logical connections depicted in FIG. 46 include a network 4671, such local area network (LAN) or a wide area network (WAN), but can also include other networks/buses. Such networking environments are commonplace in homes, offices, enterprise-wide computer networks, intranets and the Internet.

Referring now to FIG. 47, illustrated is a schematic diagram of an exemplary networked or distributed computing environment 4700. The computer 4610 of FIG. 46 can be operational in the network of FIG. 47. The distributed computing environment comprises computing objects 4710, 4712, etc. and computing objects or devices 4720, 4722, 4724, 4726, 4728, etc., which can include programs, methods, data stores, programmable logic, etc., as represented by applications 4730, 4732, 4734, 4736, 4738. It can be appreciated that objects 4710, 4712, etc. and computing objects or devices 4720, 4722, 4724, 4726, 4728, etc. can comprise different devices, such as remote controllers, PDAs, audio/video devices, mobile phones, MP3 players, laptops, etc.

Each object 4710, 4712, etc. and computing objects or devices 4720, 4722, 4724, 4726, 4728, etc. can communicate with one or more other objects 4710, 4712, etc. and computing objects or devices 4720, 4722, 4724, 4726, 4728, etc. by way of the communications network 4740, either directly or indirectly. Even though illustrated as a single element in FIG. 47, network 4740 can comprise other computing objects and computing devices that provide services to the system of FIG. 47, and/or can represent multiple interconnected networks, which are not shown. Each object 4710, 4712, etc. or 4720, 4722, 4724, 4726, 4728, etc. can also contain an application, such as applications 4730, 4732, 4734, 4736, 4738, that might make use of an API, or other object, software, firmware and/or hardware, suitable for communication with various components relating to mechanical property measurement as provided in accordance with various embodiments.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the techniques as described in various embodiments.

As a further non-limiting example, various embodiments described herein apply to any handheld, portable and other computing devices and computing objects of all kinds are contemplated for use in connection with the various embodiments described herein, i.e., anywhere that a device can request pointing based services. Accordingly, the general purpose remote computer described below in FIG. 47 is but one example, and the embodiments of the subject disclosure can be implemented with any client having network/bus interoperability and interaction.

Although not required, any of the embodiments can partly be implemented via an operating system, for use by a developer of services for a device or object, and/or included within application software that operates in connection with the operable component(s). Software can be described in the general context of computer executable instructions, such as program modules, being executed by one or more computers, such as client workstations, servers or other devices. Those skilled in the art will appreciate that network interactions can be practiced with a variety of computer system configurations and protocols.

What has been described above includes examples of the embodiments of the subject disclosure. It is, of course, not possible to describe every conceivable combination of components or methods for purposes of describing the claimed subject matter, but it is to be appreciated that many further combinations and permutations of the various embodiments are possible. Accordingly, the claimed subject matter is intended to embrace all such alterations, modifications, and variations that fall within the spirit and scope of the appended claims. Further, the order in which some or all of the process blocks appear in each process should not be deemed limiting. Rather, it should be understood that some of the process blocks can be executed in a variety of orders that are not illustrated in this disclosure. Moreover, the above description of illustrated embodiments of this disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, modules, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. The aforementioned systems, devices, and circuits have been described with respect to interaction between several components and/or blocks. It can be appreciated that such systems, devices, circuits, and components and/or blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, the words "example" or "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

In addition, while an aspect may have been disclosed with respect to only one of several embodiments, such feature may be combined with one or more other features of the other embodiments as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A method, comprising:
    converting, by a system including a processor, an image sequence into an input matrix, wherein a column of the input matrix is a vectorized image related to the image sequence;
    approximating, by the system, the input matrix with a low rank matrix with a lower rank than the input matrix;
    detecting, by the system, one or more outliers of the input matrix; and
    decomposing, by the system, the input matrix as a sum of the low rank matrix, an intensity shift due to the one or more outliers, and random noise according to:

$$D=B+E+\epsilon,$$

where D is the input matrix, B is the low rank matrix, E is the intensity shift caused by the one or more outliers and $\epsilon$ is the random noise.

2. The method of claim 1, further comprising neglecting, by the system, the random noise.

3. The method of claim 1, wherein the detecting further comprises comparing an intensity of an entry of the input matrix to a corresponding intensity of the low rank matrix.

4. The method of claim 3, wherein the detecting further comprises identifying the one or more outliers in response to the intensity of the entry of the input matrix differing from the corresponding intensity of the low rank matrix.

5. The method of claim 1, further comprising minimizing, by the system, an energy function to facilitate the approximating and the detecting.

6. The method of claim 5, wherein the minimizing further comprises iterating the approximating and the detecting at least until a convergence is reached between the approximating and the detecting.

7. The method of claim 5, wherein the minimizing further comprises minimizing the energy function having a first term describing the difference between the input matrix and the low-rank matrix, a second term measuring a property of the low rank matrix and a third term measuring a property of absolute values of the one or more outliers.

8. The method of claim 7, wherein the minimizing further comprises minimizing the energy function having a fourth term assuming that pixels neighboring each other belong to a same class.

9. The method of claim 8, wherein the same class is one of outliers or non-outliers.

10. The method of claim 1, wherein the converting further comprises converting an ultrasound image sequence, a computed tomography image sequence, or a magnetic resonance imaging sequence into the input matrix.

11. A system, comprising:
    a processor, communicatively coupled to a memory, that facilitates execution of computer-executable components to perform operations, comprising:
    converting an image sequence into an input matrix, wherein a column of the input matrix is a vectorized image related to the image sequence;
    approximating the input matrix with a low rank matrix with a lower rank than the input matrix;
    detecting an outlier of the input matrix; and
    decomposing the input matrix as a sum of the low rank matrix, an intensity shift due to the outlier, and random noise according to:

$$D=B+E+\epsilon$$

where D is the input matrix, B is the low rank matrix, E is the intensity shift caused by the outlier and $\epsilon$ is the random noise.

12. The system of claim 11, wherein the operations further comprise: neglecting the random noise.

13. The system of claim 11, wherein the detecting further comprises comparing an intensity of an entry of the input matrix to a corresponding intensity of the low rank matrix.

14. The system of claim 11, wherein the detecting further comprises identifying the outlier in response to the intensity of the entry of the input matrix differing from the corresponding intensity of the low rank matrix.

15. The system of claim 11, wherein the operations further comprise: minimizing an energy function to facilitate the approximating and the detecting.

16. The system of claim 15, wherein the minimizing further comprises iterating the approximating and the detecting at least until a convergence is reached between the approximating and the detecting.

17. The system of claim 15, wherein the minimizing further comprises minimizing the energy function having a first term describing the difference between the input matrix and the low-rank matrix, a second term measuring a property of the low rank matrix and a third term measuring a property of absolute values of the outlier.

18. The system of claim 17, wherein the minimizing further comprises minimizing the energy function having a fourth term assuming that pixels neighboring each other belong to a same class, and wherein the same class is one of outlier or non-outlier.

19. The system of claim 11, wherein the converting further comprises converting an ultrasound image sequence, a computed tomography image sequence, or a magnetic resonance imaging sequence into the input matrix.

20. A non-transitory computer-readable medium having computer-executable instructions stored thereon that, in response to execution, cause a device including a processor to perform operations, comprising:
    converting an image sequence into an input matrix, wherein a column of the input matrix is a vectorized image related to the image sequence;
    approximating the input matrix with a low rank matrix with a lower rank than the input matrix;
    detecting an outlier of the input matrix; and
    decomposing the input matrix as a sum of the low rank matrix, an intensity shift due to the outlier, and a random noise according to:

$$D=B+E+\epsilon$$

where D is the input matrix, B is the low rank matrix, E is the intensity shift caused by the outlier and $\epsilon$ is the random noise.

* * * * *